(12) United States Patent
Higuma et al.

(10) Patent No.: US 6,716,161 B2
(45) Date of Patent: Apr. 6, 2004

(54) ENDOSCOPE SUITABLE FOR AUTOCLAVE STERILIZATION

(75) Inventors: Masakazu Higuma, Hachioji (JP); Yasuyuki Futatsugi, Hachioji (JP); Ichiro Nakamura, Kokubunji (JP); Yosuke Yoshimoto, Hachioji (JP); Hidetoshi Saito, Hanno (JP); Susumu Aono, Hachioji (JP); Takao Yamaguchi, Tokyo (JP); Yutaka Tatsuno, Sagamihara (JP); Takahiro Kishi, Yokohama (JP); Yasuhito Kura, Hachioji (JP); Kazutaka Nakatsuchi, Hino (JP); Takeaki Nakamura, Hino (JP)

(73) Assignee: Olympus Corporation (JP)

( * ) Notice: Subject to any disclaimer, the term of this patent is extended or adjusted under 35 U.S.C. 154(b) by 81 days.

(21) Appl. No.: 10/097,463

(22) Filed: Mar. 13, 2002

(65) Prior Publication Data

US 2002/0128539 A1 Sep. 12, 2002

Related U.S. Application Data

(63) Continuation of application No. 09/386,718, filed on Aug. 31, 1999.

(30) Foreign Application Priority Data

| Sep. 1, 1998 | (JP) | 10-247460 |
| Sep. 1, 1998 | (JP) | 10-247461 |
| Aug. 24, 1999 | (JP) | 11-237552 |
| Aug. 24, 1999 | (JP) | 11-237554 |

(51) Int. Cl.[7] ............................................. A61B 1/04
(52) U.S. Cl. .................. 600/133; 600/162; 600/169
(58) Field of Search .................. 600/133, 162, 600/163, 169

(56) References Cited

U.S. PATENT DOCUMENTS

| 4,341,205 | A | * | 7/1982 | Hosono et al. | 600/133 |
| 4,779,613 | A | * | 10/1988 | Hashiguchi et al. | 600/169 |
| 5,056,902 | A | | 10/1991 | Chinnock et al. | 359/503 |
| 5,599,278 | A | * | 2/1997 | Hibbard | 600/133 |
| 5,842,972 | A | * | 12/1998 | Wulfsberg | 600/133 |
| 6,099,467 | A | * | 8/2000 | Kehr et al. | 600/162 |
| 6,425,857 | B1 | * | 7/2002 | Rudischhauser et al. | 600/133 |
| 6,537,210 | B1 | * | 3/2003 | Wulfsberg | 600/163 |

FOREIGN PATENT DOCUMENTS

| DE | 2808099 A1 | 8/1978 |
| DE | 3708124 A1 | 9/1987 |
| DE | 19631840 A1 | 2/1998 |
| JP | 53-119188 | 10/1978 |

* cited by examiner

*Primary Examiner*—Beverly M. Flanagan
(74) *Attorney, Agent, or Firm*—Ostrolenk, Faber, Gerb & Soffen, LLP

(57) ABSTRACT

An endoscope suitable for autoclave sterilization includes an insertion section having an objective lens section disposed at the extreme end thereof for focusing a subject image and an eyepiece section located on the base end side of the inserting section and including at least an eyepiece lens. an image guide fiber is disposed in the bundle for transmitting the subject image in an observation section focused by the objective lens section. An eyepiece lens unit is disposed in the eyepiece section, the eyepiece lens unit causing the eyepiece lens to confront the base end structure whose hermetic seal level is higher than the watertight seal level of the shell of the endoscope. A focus position changing means is disposed to the eyepiece lens unit to change the focus position of the eyepiece lens. The eyepiece section is so constructed and/or assembled that the autoclave sterilization process does not cause water vapor or the like to adversely affect the operability of the eyepiece section.

36 Claims, 10 Drawing Sheets

FIG.1
FIG.2
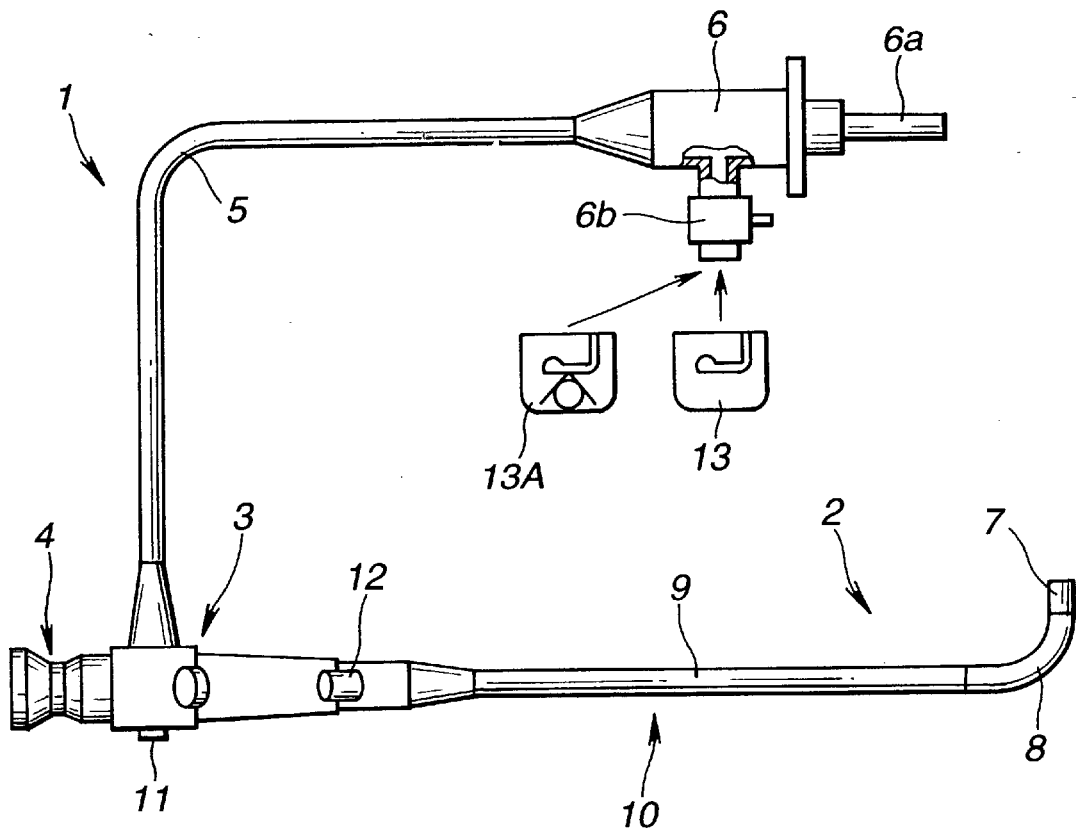
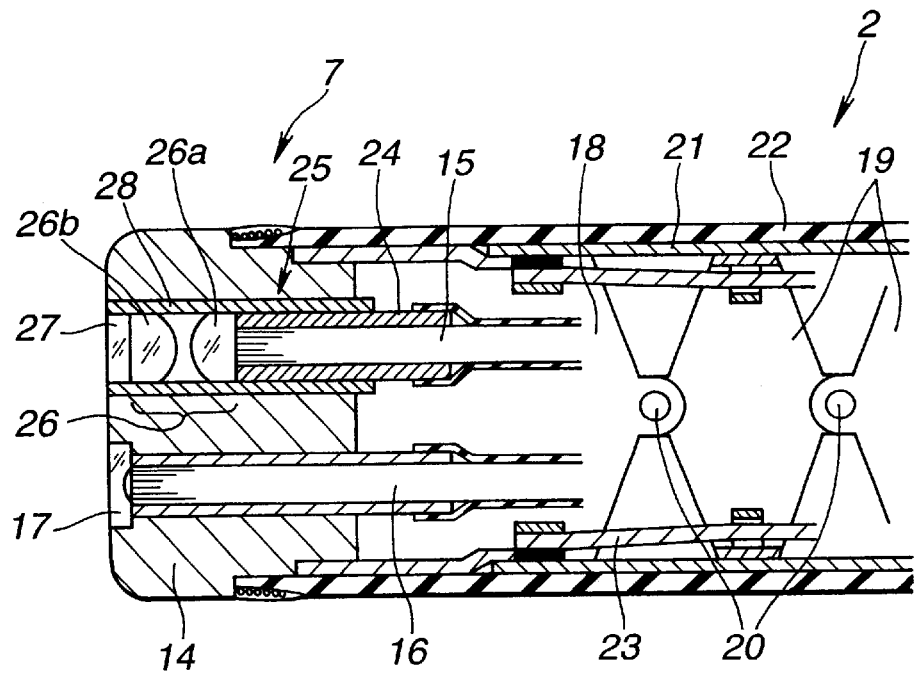

FIG.4
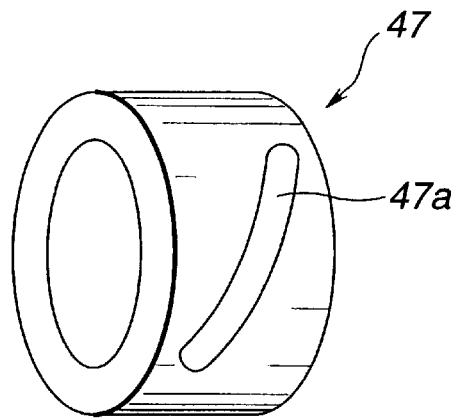
FIG.5A FIG.5B
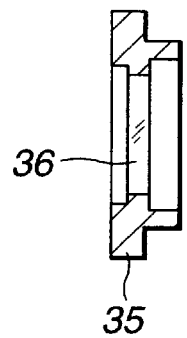 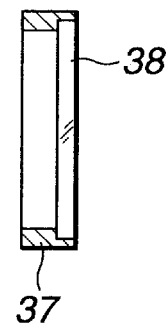
FIG.6
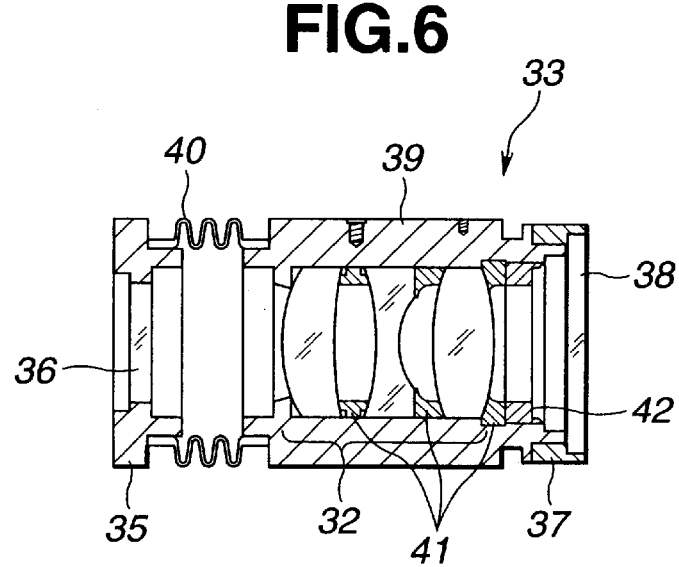

ENDOSCOPE SUITABLE FOR AUTOCLAVE STERILIZATION

RELATED APPLICATIONS

This is a continuation of U.S. patent application Ser. No. 09/386,718, filed Aug. 31, 1999, entitled ENDOSCOPE SUITABLE FOR AUTOCLAVE STERILIZATION.

BACKGROUND OF THE INVENTION

1. Field of the Invention

The present invention relates to an endoscope with an image guide fiber suitable for autoclave sterilization whose observing capability is not deteriorated by a high pressure/high temperature water vapor when the endoscope is sterilized in an autoclave.

2. Description of the Related Art

Conventionally, medical endoscopes are widely used to observe an internal organ in a cavity by inserting a slender insertion section into the cavity and to perform various kinds of medical treatments using medical instruments inserted through a medical instrument channel when necessary. Further, industrial endoscopes capable of observing and inspecting the flaw, corrosion and the like in the interior of boilers, turbines, engines, chemical plants and the like are widely used in industrial fields.

In particular, the endoscopes employed in the medical field are used to observe internal organs and the like by inserting the insertion sections into the cavity and to apply various kinds of cures and perform various kinds of treatments using treatment instruments inserted into the treatment instrument channels of the endoscopes. Thus, when an endoscope and a treatment instrument, which were used once on a patient, are used again on another patient, they must be rinsed and disinfected after the completion of patient inspection and treatment to prevent infections spreading between patients.

A gas such as an ethylene oxide gas (EOG) and the like and an antiseptic solution are used to disinfect and sterilize these endoscopes and the accessories thereof. As is well known, however, there is a problem that the sterilizing gas is highly poisonous and the sterilization process is therefore complicated. Further, a long aeration time is needed for removing the gas deposited on equipment after sterilization. Further, there is a problem that the equipment cannot be used just after it is sterilized. Furthermore, the adverse effect of the gas on the environment is a problem. In addition, the sterilization process is expensive. In contrast, using an antiseptic solution, presents the problem that the management thereof is troublesome and a large cost is required to dispose of used materials.

To cope with the above problems, recently, autoclave sterilization (sterilization by means of high pressure water vapor) is mainly used to disinfect endoscopes because it does not require a troublesome job and permits the use of the endoscopes just after they are sterilized. Further, the running cost is less expensive. The typical conditions for the autoclave sterilization are stipulated by American standards ANSI/AAMI ST 37-1992 approved by American National Standards Institute and issued by Medical Instrument Development Association. According to the conditions, the sterilizing process is carried out at 132° C. for 4 minutes~in a prevacuum type and at 132° C. for 10 minutes in a gravity type. In an ordinary autoclave sterilizing process, the temperature is set to 115° C. to 140° C. and a pressure is set +0.2 MPa with respect to the atmospheric pressure, while the actual conditions vary in different countries.

However, the high pressure/high temperature water vapor in the aforesaid conditions has the property that it is permeable to a material and adhesive mainly composed of a polymeric material such as rubber, elastomer, resin and the like. In particular, the flexible material such as the rubber, elastomer and the like are generally liable to cause water vapor to pass therethrough. In particular, a silicone rubber material has a very high water vapor permeability.

Consequently, in the conventional endoscopes whose water tight structure is constructed using a silicone rubber O-ring, a silicone rubber adhesive and the like, there is a possibility that a high pressure/high temperature water vapor penetrates into the interiors of the endoscopes in the autoclave sterilization and waterdrops remain in the interiors thereof.

Further, water vapor is also permeable even to a fluorine rubber O-ring, an epoxy adhesive and further to various kinds of other polymeric materials, in addition to the silicone rubber, although their degree of permeability is lower than that of the silicone rubber. That is, to prevent the penetration of the water vapor into the interior of the endoscope in the autoclave sterilization, the airtightness, which is required in the endoscope, is much higher than the water tightness which prevents the penetration of a conventional liquid medicine into the endoscope even if it is immersed in it, the airtightness in the ordinary atmospheric pressure and the like.

Ordinary materials used to make a high pressure/high temperature water vapor unpermeable under the conditions stipulated by the American National Standards are limited only to a material selected from metal, ceramics, glass and crystalline material. A joint means for jointing materials to each other is limited only to a joint method, for example, soldering and so forth in which a joint section is mainly composed of metal, ceramics, glass, and crystalline material.

Note that in the prevacuum type autoclave sterilization, a prevacuum process is employed as a pressure reducing process to penetrate a water vapor into the detailed sections of equipment prior to a sterilizing process. When an endoscope with an insertion section having a curved portion is to be subjected to the prevacuum type autoclave sterilization, it is an ordinary practice to perform the autoclave sterilization while communicating the exterior of the endoscope with the interior thereof to prevent the breakage of the outer sheath tube of the curved portion. As a result, the high pressure/high temperature water vapor passively penetrates into the interior of the endoscope through the communicating portion in the autoclave sterilization.

Further, many of multi-component glasses having excellent processability made of ordinary lens glass material are deteriorated by the high pressure/high temperature water vapor. Consequently, there is a possibility that the lens glass material itself is deteriorated by the penetration of the water vapor into the interior of the endoscope. Thereby, the field of vision deteriorated.

For example, in the eyepiece of the endoscope disclosed in Japanese Unexamined Utility model Publication No. 63-180821, the eyepiece visibility adjustment ring is mounted watertightly through an O-ring so that visibility can be adjusted by moving an eyepiece lens in an optical-axis direction by actuating the eyepiece visibility adjustment ring.

When the endoscope is sterilized in an autoclave apparatus, the high pressure/high temperature water vapor penetrates into the interior of the eyepiece section through the O-ring and reaches the inner surface of a cover glass, the back surface of the eyepiece lens and the end surface of an image guide fiber. Thus, there is a possibility that when the endoscope is taken out and used for observation after it is sterilized, a disadvantage arises in that the endoscope is frosted and seems to be covered with white mist.

When the autoclave sterilization is carried out for a long time or repeatedly, there is a possibility that the observing capability of the endoscope is greatly damaged by the deposition of waterdrops on the inner surface of the cover glass, the surface of a lens, and the end surface of the image fiber glass and by the deterioration of the lens glass.

Further, Japanese Unexamined Patent Publication No. 62-212614 discloses a hard endoscope having a hard insertion section in which an observation optical system including an eyepiece lens is arranged airtightly. However, in this endoscope, the visibility of the eyepiece section cannot be adjusted. Thus, when this arrangement is applied to an endoscope using an image guide fiber, there is caused an disadvantage that visibility is not properly set and observation is obstructed depending upon observers. In the endoscope using the image guide fiber, an eyepiece lens must be accurately focused on the end surface of the image guide fiber from which an image is projected regardless of whether a hard mirror or a soft mirror is used. That is, the endoscope is arranged such that an observer can obtain a best subject image by performing visibility adjustment in accordance with his or her vision.

That is, the arrangement of the hard endoscope disclosed in Japanese Unexamined Patent Publication No. 62-212614 is limited only to the hard endoscope having the hard insertion section which employs a relay lens as an image transfer means which does not need the visibility adjustment of the eyepiece section.

In the hard endoscope, since an optical member such as a lens, a cover glass and the like is bonded to a frame member with the adhesive, it is actually difficult to obtain an effect for shutting off a water vapor having a too much higher pressure and temperature. That is, when autoclave sterilization is performed under the conditions stipulated by the American Standards and the like, a water vapor penetrates into the interior of an observation optical system through the adhesive.

To cope with this problem, in the hard endoscope with a hard insertion section disclosed in DE19631840A1, a housing constituting the shell of the endoscope is composed of metal so far as it is possible as well as the joints between components are airtightly jointed to each other by soldering or the like. With this arrangement, the endoscope can be arranged airtightly into which no high pressure/high temperature water vapor penetrates from an autoclave through the shell thereof. In the arrangement of the hard endoscope, the focal length of an optical system can be adjusted by moving a lens disposed in the interior of the airtightly-sealed endoscope by deforming a deformable wall region disposed on the shell of the endoscope.

However, in an endoscope whose insertion section has, for example, a curved portion, the outer sheath tube of the curved portion is composed of a polymeric material such as rubber, elastomer and the like which are flexible. Also in the endoscope with the curved portion, a rubber seal member such an O-ring and the like is used to hermetically seal the rotary shaft of an operation lever for curving the curved portion. Further, even in an endoscope without a curved portion to its insertion section, when the insertion section is flexible, a flexible polymeric material is also used as the outer sheath tube of the inserting section.

Therefore, in a soft endoscope with an insertion section at least a portion of which is composed of a soft material, at least a portion of the shell of the endoscope is composed of a polymeric material. Accordingly, it is impossible to perfectly hermetically seal the entire shell thereof airtightly as shown in DE19631840A1. That is, a high pressure/high temperature water vapor gradually penetrates into the interior of the soft endoscope in the autoclave sterilization.

As described above, the arrangement of the endoscope disclosed in DE19631840A1 is limited only to the hard endoscope whose entire shell can be arranged airtightly by using an insertion section composed of metal or ceramics.

Further, in DE19631840A1, the deformable wall region for adjusting the focal length of the optical system, that is, the visibility adjusting operation section is also a portion of the shell of the endoscope. Accordingly, the visibility adjusting operation section must be composed of a metal material or the like into which a water vapor does not penetrate such as a metal bellows or the like, to which a metal thin film and a lever are disposed, to maintain airtightness. Therefore, the operability in the adjustment of the focal length of the optical system is lowered as compared with the operability in the adjustment of the focal length performed by means of the visibility adjustment ring disclosed in Japanese Unexamined Utility Model Publication No. 63-180821.

Further, the deformable wall region must be airtightly jointed as the shell of the endoscope by soldering or the like. In addition, the joints between the other components of the shell of the endoscope must be airtightly jointed by soldering or the like. Thus, there is a problem that not only the assembling of the endoscope is very poor but also when the endoscope is assembled once, it is almost impossible to repair the inner components therein, or readjustment of the visibility adjustment member or the like by removing a portion of the shell.

SUMMARY OF THE INVENTION

An object of the present invention is to provide an endoscope suitable for autoclave sterilization including an image guide fiber as an image transmission means whose observing capability is not deteriorated even if it is exposed to high pressure/high temperature water vapor.

Another object of the present invention is to provide an endoscope suitable for autoclave sterilization including an image guide fiber through which an observer can observe the subject image of an observation section which is transmitted through the image guide fiber under best conditions by adjusting the visibility thereof in accordance with his or her vision.

Still another object of the present invention is to provide an endoscope suitable for autoclave sterilization including an image guide fiber which can be easily assembled and repaired.

A further object of the present invention is to provide an endoscope suitable for autoclave sterilization including an image guide fiber which has excellent operability in visibility adjustment.

Briefly, an endoscope of the present invention suitable for autoclave sterilization includes an inserting section having an objective lens section disposed at the extreme end thereof for focusing a subject image and an eyepiece section located at the base end side of the inserting section and including at least an eyepiece lens. An image guide fiber is disposed in the inserting section which is composed of an optical fiber bundle for transmitting the subject image in an observation section focused by the objective lens section, and an eyepiece lens unit is disposed in the eyepiece section, the eyepiece lens unit causing the eyepiece lens to confront the base end surface of the image guide fiber and having a hermetic seal structure whose hermetic seal level is higher than the watertight seal level of the shell of the endoscope. A focus position changing means is disposed at the eyepiece lens unit to change the focus position of the eyepiece lens.

BRIEF DESCRIPTION OF THE DRAWINGS

FIG. 1 to FIG. 7 are views explaining a first embodiment of the present invention: wherein, FIG. 1 is a view explaining an arrangement of an endoscope;

FIG. 2 is a view explaining an arrangement of the vicinity of the extreme end of the insertion section of the endoscope;

FIG. 4 is a view explaining an associating frame;

FIG. 5A is a view showing a state in which an extreme end cover glass is disposed at an extreme end cover glass frame;

FIG. 5B is a view showing a state in which a base end cover glass is disposed at a base end cover glass frame;

FIG. 6 is a view explaining an arrangement of the eyepiece lens unit; and

FIG. 7 is a view explaining the relationship between the eyepiece lens unit and an endoscope main body, FIG. 9 and FIG. 10 show still another arrangement of the eyepiece section: wherein FIG. 9 is a view explaining another arrangement of the eyepiece lens unit;

FIG. 10 explains a volume change adsorbing member disposed to an eyepiece unit, wherein FIG. 12 and FIG. 13 are views explaining a second embodiment of the present invention: wherein FIG. 12 is a view explaining an arrangement of a eyepiece section; and FIG. 13 is a conceptual view of a liquid crystal lens, FIG. 14 and FIG. 15 show a further arrangement of the eyepiece lens unit: wherein FIG. 14 is a view explaining a further arrangement of the eyepiece unit;

FIG. 15A and FIG. 15B conceptually explain a variable focus lens, wherein

FIG. 15A is a view explaining a difference of operation when the focal position of the variable focus lens is changed and FIG. 15B is a view explaining a difference of operation when the focal position of the variable focus lens is changed.

DESCRIPTION OF THE PREFERRED EMBODIMENTS

Figure 3A:
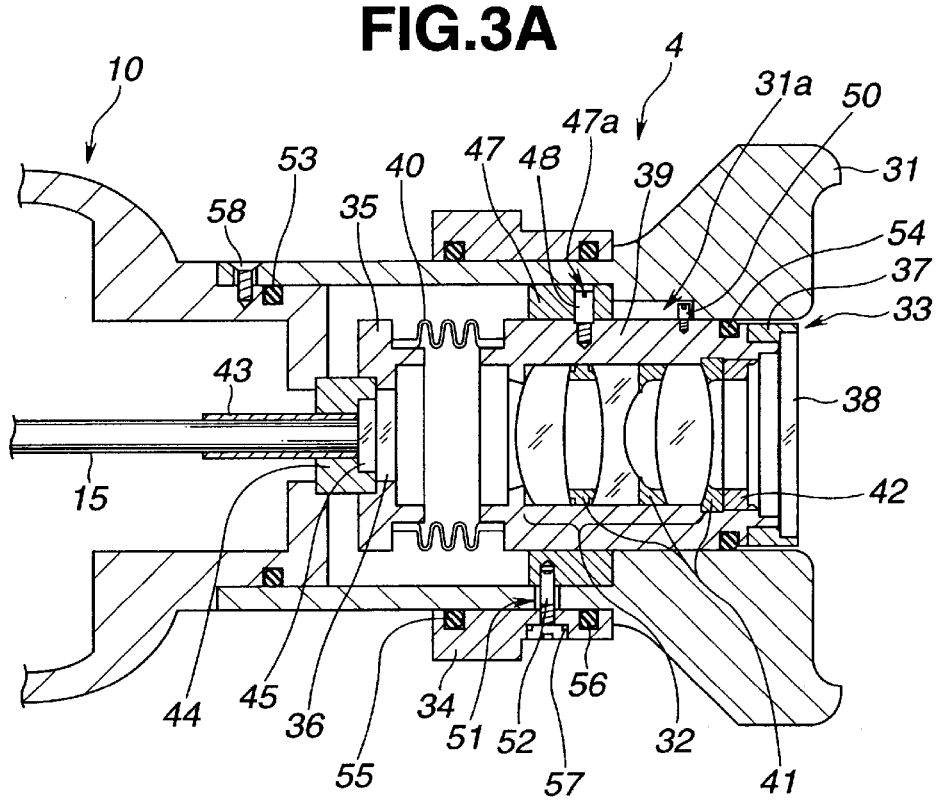
FIG. 3A is a view showing an example of an eyepiece section.

An embodiment of the present invention will be described with reference to FIG. 1 to FIG. 7.

As shown in FIG. 1, an endoscope 1 of the embodiment mainly comprises an insertion section 2 into which is inserted an image guide fiber composed of an optical fiber bundle denoted by a numeral 15 shown in FIG. 2 to be described later, an operating section 3 disposed on the base end side of the insertion section 2 and grasped by an operator for various kinds of operations, an eyepiece section 4 disposed on an end of the operating section 3, and a universal code 5 extending from a side of the operating section 3. A connector section 6 having a light guide connector 6a, which is connected to a light source (not shown), is disposed at the other end of the universal code 5.

The internal spaces of the insertion section 2, the operating section 3, the universal code 5 and the connector section 6 communicate with each other. With this arrangement, one endoscope internal space (also described simply as an internal space) is formed to the shell of the endoscope. Further, an outer sheath tube composed of a flexible rubber material such as a silicone rubber tube or the like is used for the sheath of the universal code 5 because it is flexible and light and can be handled easily. Further, in the present invention, the insertion section 2, in which the image guide fiber is disposed, and the operating section 3 are identified as an endoscope main body (hereinafter, the "main body") 10 as a whole.

The insertion section 2 is composed of an extreme end portion 7, a curving portion 8 which can be optionally curved and a flexible tube 9 having flexibility.

A rubber material such as fluorine rubber and the like or thermoplastic elastomer, which has high strength and flexibility even if it is thin, is used as an outer sheath tube constituting the sheath of the curving portion 8.

Flexible thermoplastic elastomer such as polyester elastomer, polyamide elastomer and the like is used as the sheath material of the flexible tube 9 to obtain suitable flexibility.

The operating section 3 is provided with a curving operation lever 11 for controlling the operation of the curving portion 8, a treatment tool inserting port 12 into which a treatment tool such as a clamp and the like is inserted and so forth. The curving operation lever 11 is assembled rotatably and watertightly using an O-ring (not shown) made of silicone rubber or fluorine rubber.

A ventilation mouthpiece 6b is disposed to the connector section 6 to communicate the inner space of the endoscope 1 to the outside. A ventilation cap 13, mounted on the ventilation mouthpiece 6b as shown by an arrow permits the outside of the endoscope shell to communicate with the inside thereof, that is, the inner space of the endoscope 1 to communicate with the outside thereof.

In autoclave sterilization, the endoscope 1 is placed in the chamber of an autoclave sterilizing apparatus in a state in which the ventilation cap 13 is mounted on the ventilation mouthpiece 6b. The inner space of the endoscope 1 is communicated with the outside thereby so that the breakage of the outer sheath tube constituting the curving portion 8, and the like can be prevented.

Note that unless the ventilation mouthpiece 6b is in the communicating state, the inner space of the endoscope 1 is not communicated with the outside thereof. That is, the endoscope 1 is arranged to have such a watertight structure that when the endoscope 1 is immersed into a liquid medicine, it does not penetrate into the inner space of the endoscope 1.

Further, as described above, in the endoscope 1 having the soft insertion section 2 and in the endoscope 1 having the curving portion 8, a polymeric material such as rubber, thermoplastic elastomer or the like is used as a member for constituting the shell of the endoscope 1 and as a hermetic seal member. Thus, it is impossible to perfectly prevent the penetration of a water vapor into the inner space of the endoscope 1.

In the endoscope 1, an extreme end main body 14 formed of a hard material is disposed to the extreme end portion 7 of the insertion section 2 as shown in FIG. 2. Assembled to the extreme end main body 14 is an image guide fiber 15 constituting an observation optical system and a light guide fiber 16 constituting an illumination optical system. An illumination lens 17 is fixed through an adhesive to the extreme end main body 14 on the extreme end surface of the light guide fiber 16.

An extreme-end-curved piece 18, which constitutes the curving portion 8, is fixed to the base end of the extreme end main body 14, and a plurality of curved pieces 19, . . . , 19 are further rotatably connected to the base end of the extreme-end-curved piece 18 by rivets 20.

The outer peripheries of the extreme-end-curved piece 18 and the plurality of curved pieces 19, . . . , 19 are covered with metal net tubes 21. The outer peripheries of the metal net tubes 21 are further covered with outer sheath tubes 22 as outer skin materials made of fluorine rubber. In addition, the extreme end of a curving wire 23 is fixed to the extreme-end-curved piece 18 by brazing to pull and curve the curving portion 8 by operating the curving operation lever 11.

In contrast, both the ends of the image guide fiber 15 are hardened by acid-dissolved glass in a state in which fiber strands disposed to the extreme end thereof are aligned with fiber strands disposed to the base end thereof. Airtightness is established between the fiber strands at the ends of the image guide fiber 15 hardened by the acid-dissolved glass. Further, the strands each having a core and a clad are disposed in a loosened state at the intermediate portion of the image guide fiber 15 so as to enhance the bending property thereof.

The extreme end of the image guide fiber 15 is airtightly jointed to a metal image guide fiber frame 24, which is an airtight partition member having a resistance to a high pressure/high temperature water vapor, by molten glass. Then, a base end lens 26a, which constitutes the objective lens group 26 of an objective lens section 25, is bonded and fixed to the extreme end surface of the image guide fiber 15 by a translucent adhesive.

An objective cover glass 27 disposed to the forefront end of the objective lens section 25 is made of sapphire acting as an airtight partition member. The outer peripheral surface of the objective cover glass 27 is subjected to a surface treatment such as a metallizing treatment to permit the objective cover glass 27 to be airtightly jointed to a metal objective lens frame 28. With this arrangement, the objective cover glass 27 is airtightly jointed to the objective lens frame 28 by soldering.

The surface treatment applied to the outer peripheral surface of the objective cover glass 27 is a treatment called metallizing which renders the surface of a non-metallic member metal-like. Examples of the metallizing treatments include, for example, the surface treatment obtained by the sequential vapor deposition of chromium, nickel and gold, and the like.

The respective layers may be formed by sputtering, ion plating, plating and the like, in addition to the vapor deposition. Further, various kinds of materials may be used as the material for constituting the respective layers, in addition to the above materials. It is preferable that a gold layer or the like be formed at a metal part to be soldered such as the metal objective lens frame 28 to improve the wettability thereof with a solder.

The extreme end lens 26b of the objective lens group 26 is inserted into and fixed in the interior of the objective lens frame 28 to which the objective cover glass 27 is jointed airtightly. Then, the image guide fiber frame 24, to which the image guide fiber 15 having the base end lens 26a of the objective lens group 26 bonded thereto is disposed, is inserted into the interior of the objective lens frame 28. Then, the insertion of the image guide fiber frame 24 is stopped at a sharply-focused position, and the image guide fiber frame 24 is tentatively fixed to the objective lens frame 28 by spot welding. Thereafter, the objective lens frame 28 is airtightly jointed to the image guide fiber frame 24 by, for example, laser welding.

The laser welding is applied to the entire periphery of the objective lens frame 28 from the outer peripheral side thereof so as to airtightly join the parts to each other. With these operations, since the portion comprising the objective cover glass 27, the objective lens frame 28, the image guide fiber frame 24 and the end of the image guide fiber 15 is airtightly sealed with the airtight partition member and the airtight joint means, no water vapor penetrates into the airtightly-sealed section when autoclave sterilization is carried out.

Note that the image guide fiber 15 is not limited to the flexible fiber bundle the extreme end and the base end of which are hardened by the acid-dissolved glass and the intermediate portion of which is composed of the loosened strands each having the core and the clad as described above. That is, the image guide fiber 15 may be, for example, a conduit fiber arranged as a single conduit over the entire length thereof and has a plurality of core glasses disposed in a clad glass. Further, the flexible fiber bundle is often composed of multi-component glass, and the conduit fiber may be composed of quartz glass and the like, in addition to the multi-component glass.

Figure 3B:
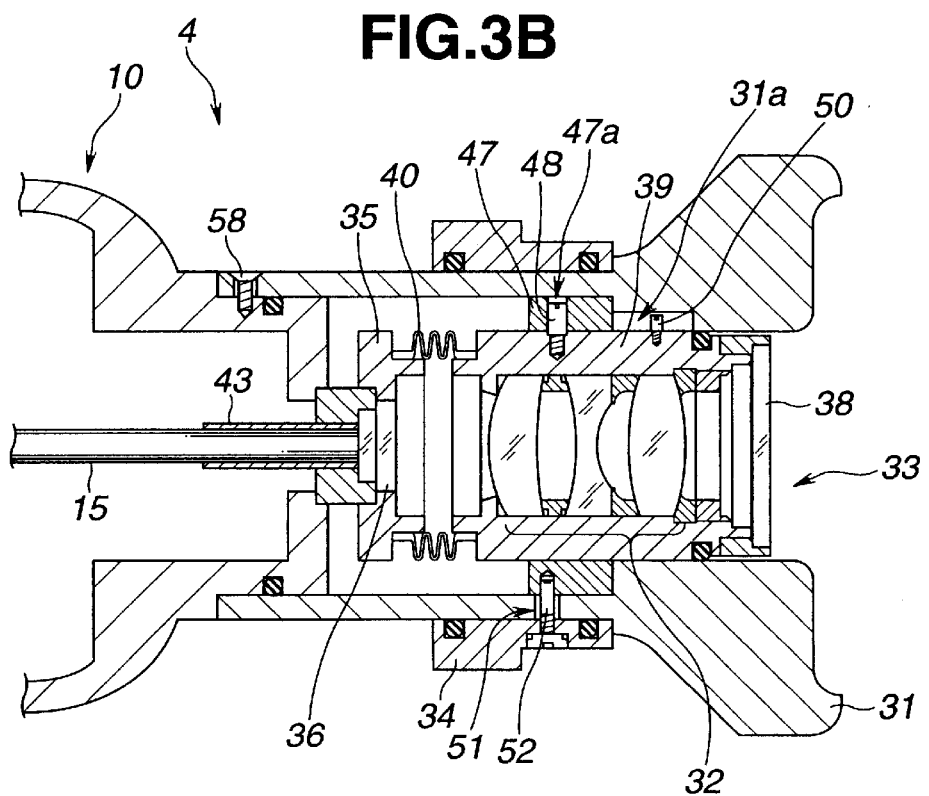
FIG. 3B is a view showing a state in which an eyepiece lens unit disposed in the eyepiece section is moved toward an extreme end.

As shown in FIG. 3A and FIG. 3B, the eyepiece section 4 mainly comprises an eyepiece 31 fixed to the operating section 3 of the main body 10, an eyepiece lens unit 33 disposed in the eyepiece 31 and having an eyepiece lens group 32 composed of at least one optical member, and a visibility adjustment ring 34 acting as a visibility adjusting operation unit for performing the positional adjustment of the focal position variable means of the eyepiece lens group 32.

The base end of the image guide fiber 15 extending from the extreme end portion 7, that is, an image output end is disposed at the extreme end of the eyepiece lens unit 33.

The eyepiece lens unit 33 comprises an extreme end cover glass frame 35 made of metal and acting as an airtight partition member, an extreme end cover glass 36 made of sapphire and acting as an airtight partition member, a base end cover glass frame 37 made of metal and acting as an airtight partition member, a base end cover glass 38 made of sapphire and acting as an airtight partition member, an eyepiece lens frame 39 made of metal and acting as an airtight partition member, a bellows 40 made of metal and the eyepiece lens group 32. The extreme end cover glass 36 is airtightly jointed to the extreme end cover glass frame 35; the base end cover glass 38 is airtightly jointed to the base end cover glass frame 37; the eyepiece lens frame 39 is airtightly jointed to base end cover glass frame 37; the bellows 40 is a tube-like elastic airtight partition member acting as a focal position variable means, which is airtightly jointed to the eyepiece lens frame 39 and the extreme end cover glass frame 35 at both the ends thereof and can be extended and contracted in an optical-axis direction; and the eyepiece lens group 32 is disposed in the eyepiece lens frame 39.

The eyepiece lens group 32 is fixedly disposed at a predetermined position in the eyepiece lens frame 39 by an interval ring 41 and a presser member 42. The extreme end cover glass 36 and the base end cover glass 38 act as the extreme end optical window and the base end optical window of the eyepiece lens unit 33, respectively.

Used as the bellows 40 is, for example, a metal vacuum flexible bellows which is a tubular material expandable in the optical-axis direction, capable of maintaining airtightness and usable in, for example, vacuum piping, and the like. Exemplified as the vacuum flexible bellows are bellows composed of a plurality of welded metal disc members, a bellows composed of a metal integrally formed to a bellows shape, and the like.

The base end of the image guide fiber 15 is located at a position nearer to the foremost end of the extreme end cover glass frame 36. A base end image guide fiber frame 43 is, for example, bonded and fixed to the outer periphery of the base end of the image guide fiber 15, and a fiber cover glass frame 44 is bonded and fixed to the outer periphery of the base end of the base end image guide fiber frame 43. A fiber cover glass 45 is bonded and fixed to the fiber cover glass frame 44. The fiber cover glass 45 is bonded and fixed to the base end surface of the image guide fiber 15 by a translucent adhesive without forming an air layer therebetween. Then, the fiber cover glass 45 is also bonded and fixed to the extreme end cover glass 36 of the eyepiece lens unit 33 by a translucent adhesive without forming an air layer therebetween.

Note that the fiber cover glass frame 44 is bonded and fixed to the main body 10.

As shown in FIG. 4, an associating frame 47 having a cam hole 47a formed obliquely with respect to a circumferential direction is fitted on the outer periphery of the eyepiece lens frame 39 of the eyepiece lens unit 33. A cam pin 48, which is attached to the eyepiece lens frame 39, is engaged with the cam hole 47a.

A rotation regulating groove 31a for regulating the rotation of the eyepiece lens unit 33 is formed at the inner peripheral surface of the eyepiece 31. A rotation stop pin 50 attached to the eyepiece lens frame 39 is inserted into and disposed to the rotation regulating groove 31a.

Further, a peripherally-directed through hole 51 is formed at the side periphery of the eyepiece 31. A fixing pin 52 for fixing the visibility adjustment ring 34 is inserted into and disposed at the peripherally-directed through hole 51. The visibility adjustment ring 34 is fixed to the associating frame 47 integrally therewith by fixing the fixing pin 52 to the associating frame 47.

With this arrangement, the rotation of the visibility adjustment ring 34 causes the simultaneous rotation of the associating frame 47 which is coupled and fixed to the visibility adjustment ring 34 through the fixing pin 52. Then, the cam pin 48, which is engaged with the cam hole 47a of the associating frame 47, is moved in the optical-axis direction by the rotation of the associating frame 47 as shown in FIG. 3B, and the bellows 40 is contracted by the movement of the eyepiece lens frame 39, in which the eyepiece lens group 32 is disposed, in, for example, the extreme end direction of the optical-axis direction. At the time, the interior of the eyepiece lens unit 33 is maintained in an airtight state.

Note that since the rotation stop pin 50 is inserted into the rotation regulating groove 31a of the eyepiece 31, the eyepiece lens frame 39 is not rotated. Further, O-rings 53, 54, 55, 56 and 57 for maintaining water tightness are interposed between the respective components, that is, between the main body 10 of the endoscope 1 and the eyepiece 31, between the eyepiece 31 and the eyepiece lens unit 33, between the eyepiece 31 and the visibility adjustment ring 34, and between the visibility adjustment ring 34 and the fixing pin 52. With this arrangement, when the endoscope 1 is rinsed or immersed into the liquid medicine, the penetration of a fluid into the eyepiece section 4 is prevented.

The detailed arrangement of the eyepiece lens unit 33 and a method of assembling the eyepiece section 4 will be described with reference to FIG. 5 to FIG. 7.

First, the extreme end cover glass frame 35 is airtightly jointed to the extreme end cover glass 36 as shown in FIG. 5A and the base end cover glass frame 37 is airtightly jointed to the base end cover glass 38 as shown in FIG. 5B, respectively by soldering or brazing. Note that the aforesaid metallizing treatment is applied to the outer peripheral surfaces of the extreme end cover glass 36 and the base end cover glass 38.

Next, as shown in FIG. 6, the base end cover glass frame 37 is airtightly jointed by laser welding to the base end of the eyepiece lens frame 39, which is disposed to and fixed at a predetermined position by the interval ring 41 and the presser member 42 and provided with the eyepiece lens group 32.

Next, one end of the metal bellows 40 is airtightly jointed to the extreme end cover glass frame 35 by laser welding. Then, the other end of the bellows 40 is airtightly jointed to the extreme end of the eyepiece lens frame 39 by laser welding.

With the above assembling job, the inner space of the eyepiece lens unit 33, which is surrounded by the extreme end cover glass 36, the extreme end cover glass frame 35, the bellows 40, the eyepiece lens frame 39, the base end cover glass frame 37, and the base end cover glass 38, is arranged as an airtightly-sealed section. This is because the respective members, which are composed of the metal members and the sapphire which act as the airtight partition members, are jointed to each other by the airtight joint means such as the soldering, laser welding and the like.

Note that the eyepiece lens unit 33, which is composed of the substantially rigid metal members and the sapphire which act as the airtight partition members, is arranged very rigidly. Thus, the eyepiece lens unit 33 is strong enough not to be broken in the autoclave apparatus even if it is pressurized and depressurized therein.

Figure 7:
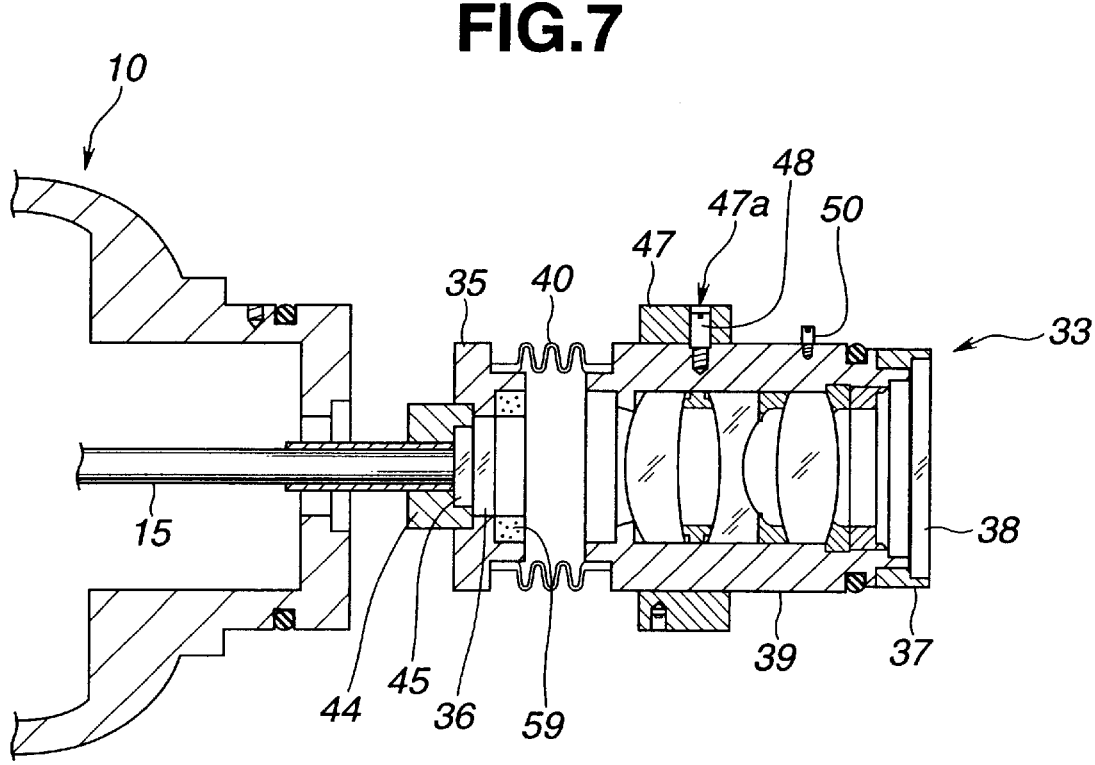

Subsequently, the associating frame 47 is fitted on the outer peripheral surface of the eyepiece lens frame 39 which constitutes the eyepiece lens unit 33 as shown in FIG. 7 and the cam pin 48 is screwed in and fixed to the eyepiece lens frame 39 through the cam hole 47a of the associating frame 47. Thereafter, the rotation stop pin 50 is screwed in and fixed to the eyepiece lens frame 39 at a predetermined position thereof.

Next, the base end of the image guide fiber 15 is drawn out from the main body 10 of the endoscope 1, and the fiber cover glass 45 fixed to the fiber cover glass frame 44 is bonded and fixed to the base end surface of the image guide fiber 15 by a translucent adhesive without forming an air layer therebetween.

Next, the fiber cover glass 45 is bonded and fixed to the extreme end cover glass 36 of the airtightly sealed eyepiece lens unit 33 by a translucent adhesive without forming an air layer therebetween. With this arrangement, water vapor is prevented from permeating into the light passage through any portions thereof, which ranges from the base end surface of the image guide fiber 15, that is, the image projecting end thereof to the base end cover glass 38 corresponding to the base end optical window of the airtightly sealed eyepiece lens unit 33.

As shown in FIG. 3A, after the fiber cover glass frame 44 in this state is bonded and fixed to the main body 10, the rotation stop pin 50 is inserted into and connected to the rotation regulating groove 31a of the eyepiece 31, and the eyepiece 31 is slid from a rear side toward an extreme end side and disposed so as to cover the outer periphery of the eyepiece lens unit 33. Finally, the eyepiece 31 is integrally fixed to the main body 10 by a screw 58.

At this time, the visibility adjustment ring 34 has been previously fitted on the outer periphery of the eyepiece 31. Thus, the assembly of the eyepiece section 4 is completed by fixing the visibility adjustment ring 34 to the associating frame 47 integrally with each other by the fixing pin 52 through the peripherally-directed through hole 51 formed at the eyepiece 31.

In addition to the assembling procedure of the eyepiece section 4, the assembling procedure and the like of the shell of the endoscope are similar to those of a conventional endoscope, and shell members are maintained watertightly by O-rings, adhesives and so on.

More specifically, in the endoscope 1 of the embodiment arranged as described above, since only the eyepiece lens unit 33 acting as a portion of the observation optical system and the objective lens section 25 are airtightly sealed, the components other than the above components can be assembled similarly to conventional endoscopes. Therefore, endoscopes of the embodiment can be assembled as easily as the conventional endoscope. Further, in the embodiment, the visibility adjusting operation section for adjusting visibility is not arranged as a part of the partition members for constituting the airtightly sealed space. Accordingly, the endoscope of the presently described embodiment has excellent operability because it can employ a visibility adjustment ring system for securing the water tightness only in the eyepiece section 4 by means of the O-rings 55, 56 and 57 similarly to conventional endoscopes.

The operation of the endoscope 1 of the present embodiment is described below.

When the endoscope 1 is used, an observer observes a subject image focused through the objective lens group 26 by looking through the eyepiece section 4. The subject image is focused on the image incident end surface of the image guide fiber 15, which is the extreme end surface thereof, by the objective lens section 25 of the extreme end portion 7 and transmitted to the image projecting end surface of the image guide fiber 15 as the base end surface thereof by the image guide fiber 15 which passes through the insertion section 2.

The subject image transmitted up to the base end surface of the image guide fiber 15 is enlarged by the eyepiece lens group 32 and observed by the observer. If the focal position of the eyepiece lens group 32 is not matched with the base end surface of the image guide fiber 15, the subject image is unfocused and a sharp subject image cannot be obtained.

Further, not all observers have the same vision acuity. Thus, the focal position of the eyepiece lens group 32 must be adjusted for different observers.

When the visibility is to be adjusted, the observer rotates the visibility adjustment ring 34. The associating frame 47 coupled to the visibility adjustment ring 34 through the fixing pin 52 is rotated by the rotation of the visibility adjustment ring 34. As a result, the focal position is adjusted by the axially directed, forward and rearward movement of the eyepiece lens frame 39 having the eyepiece lens group 32 disposed therein as described above.

The expansion and contraction of the bellows 40 permits the eyepiece lens frame 39 to move in the optical-axis direction in a manner which maintain the interior of the eyepiece lens unit 33 airtight.

Note that the visibility is adjusted not only when an observer performs a visual observation but also when the image input means of an external photographing apparatus is mounted on the eyepiece section 4. That is, when, for example, the subject image on the projecting surface of the image guide fiber is to be focused on the solid state imaging device of an externally-mounting type camera, the focal position of the eyepiece lens group 32 is adjusted by operating the visibility adjustment ring 34. With this operation, a best subject image can be displayed on a monitor (not shown).

After the endoscope 1 has been used for observing a patient as described above, it is subsequently subjected to autoclave sterilization. In prevacuum type autoclave sterilization procedures, a pressure difference arises between the outside of the airtightly sealed eyepiece lens unit 33 and the inside thereof.

Consequently, the endoscope 1 is exposed to a high pressure/high temperature water vapor in the sterilizing process. During the process, the high pressure/high temperature water vapor gradually penetrates the interior of the endoscope 1 through the members composed of the polymeric material such as the outer sheath tube 22 of the curving portion 8, and the like which constitute the shell of the endoscope. Further, when the outside of the endoscope 1 is communicated with the inside thereof, the positive high pressure/high temperature water vapor causes vapor to penetrate into the interior of the of the endoscope. At the time, the endoscope 1 is heated to about 115° C. to 140° C.

In the drying process performed thereafter, a pressure difference similar to that in the prevacuum process arises between the outside and the inside of the eyepiece lens unit 33.

As described above, in the autoclave sterilization process, the high pressure/high temperature water vapor does not penetrate into the interior of the eyepiece lens unit 33 which is sealed airtightly. Further, the eyepiece lens unit 33 is not broken by the effects of the pressure difference and the temperature change in the autoclave sterilization because it is rigidly formed and arranged. Further, when the endoscope 1 is to be repaired, for example, when the curving mechanism is to be adjusted or any of the inner parts of the endoscope 1 need to be replaced or repaired, the inner parts can be easily replaced by removing a portion of the shell of the endoscope similarly to ordinary endoscopes.

The embodiment has the following effects.

Visibility can be adjusted by an observer even if the endoscope uses the image guide fiber as the image transmission means water vapor penetration in the autoclave sterilization is reliably prevented.

An observer can adjust visibility even in the endoscope with the curving portion in which at least a portion of the endoscope shell must be composed of a polymeric material and even in an endoscope which has a flexible insertion section and employs the image guide fiber as the image transmission means. Still, a faulty field of vision resulting from the water vapor in the autoclave sterilization is reliably prevented.

Since only a portion of the observation optical system such as the eyepiece lens unit and the like constituting the eyepiece section is airtightly sealed without airtightly sealing the entire shell of the endoscope, the other parts of the endoscope can still be made similar to conventional endoscopes. As a result, not only the endoscope can be assembled as easily as the conventional endoscope but also if any of the inner parts of the endoscope fail, the failed inner parts can be easily replaced by removing only a portion of the shell of endoscopes similarly to the conventional endoscope. Thus, the endoscope of the present invention has good repair properties.

Since the visibility adjusting operation section for adjusting visibility is not arranged as a portion of the airtight partition members constituting the air tight structure, the visibility adjusting operation section having good operability is realized. The embodiment secures good operability by employing the visibility adjusting operation section of the visibility adjustment ring system similar to a conventional visibility adjustment ring system.

The airtightness of the eyepiece lens unit can be maintained as well as visibility can be adjusted by a very simple arrangement without using an electric control. That is, the endoscope used in the embodiment is a fiber type endoscope which does not basically need an electric signal. Accordingly, when the visibility adjustment is carried out without the need of the electric control, no power supply is required when the endoscope is used.

When the eyepiece optical system is arranged as a fixed focus zoom optical system, an airtight eyepiece lens unit with a variable power mechanism can be provided.

Note that it is preferable that the eyepiece lens unit in the embodiment be airtightly sealed as described above. The airtight partition member and the airtight joint means for arranging the eyepiece lens unit as the airtightly sealed structure are not limited to those described in the embodiment and the airtight partition member and the airtight joint means shown below may be used.

That is, in the embodiment, metal and sapphire are used as the materials of the airtight partition members for constituting the airtightly-sealed section of the eyepiece lens unit. These materials resist high temperature. In addition, the materials are substantially rigid bodies having such pressure resistance that they are not broken when they are pressurized or depressurized in the autoclave sterilization process. Further, since the materials have high vacuum characteristics by themselves (when the space volume in a test piece is 0.1–0.4 cm$^3$, the equivalent reference leak amount detected by a helium leak detector shown in JIS Z2332 and the like is $1\times10^{-9 Pa m3/3}$), they are materials which can be airtightly jointed. Materials which can be airtightly jointed are materials having such heat resistance which permit them to endure the heat applied thereto when they are jointed by the airtightly joint means which will be described later.

In contrast, a polymeric material such as ordinary resin, rubber and the like cannot satisfy the conditions required to the airtight partition members.

That is, the material for the airtight partition members is limited to a material mainly composed of metal, ceramics, glass and crystalline material, and a preferable material is selected therefrom. Various kinds of materials can be used the metal, and metals, for example, stainless, covar and the like can be used.

In the embodiment, ceramics and glass are described as if they are separate materials. However, ceramics is a generic term representing a nonmetal inorganic material which can be ordinarily obtained through such processes as molding, baking and the like. Thus, glass is also contained in ceramics in a broad sense. Many ceramics satisfy the conditions for constituting airtight partition materials as usable when metal cannot be used due to insulation problems, optical problems and the like. However, some ceramic materials have low vacuum characteristics, resulting in cracks when they are heated for obtaining airtight joints, and are severely deteriorated by a water vapor. Therefore, caution must be taken in the selection of ceramics. When ceramics are used as insulating materials, it is preferable to use fine ceramics having good insulation properties and high vacuum characteristics. Such ceramics are aluminum nitride, sialon, alumina, black alumina, silicon nitride and the like.

In addition, many multi-component glasses which are ordinarily used as optical members are deteriorated by water vapor. Thus, a translucent crystalline material or multi-component glass having a high resistance against a high pressure/high temperature water vapor must be used for optical members to be used as airtight partition materials, that is, as an optical window. Incidentally, sapphire is a monocrystal of $Al_2O_3$ and classified as a translucent crystalline material. That is, sapphire is a typical optical material which satisfies the conditions constituting an airtight partition material. Note that ruby, crystal (quartz) and the like are also examples of translucent crystalline materials, in addition to sapphire.

While welding in a broad sense, such as laser welding, soldering, brazing and the like, are employed to obtain airtight joints, various other joint means which employ welding making use of metal can be employed.

Examples of the welding are fusion welding represented by laser welding, electron beam welding and the like, pressure welding represented by resistance welding, and brazing welding such as soldering, brazing and the like. For example, when two metal parts, which are airtight partition materials, are jointed to each other by laser welding, the two metal parts are fused and integrated with each other, whereby the joint thereof is arranged as the airtight partition materials themselves so that airtightness can be reliably secured.

In brazing, the joint between airtight partition materials is filled with metal, whereby airtightness can be secured. While various kinds of brazing filler metal such as gold braze, silver braze, nickel braze, copper braze, etc. can be used, preferably, brazing filler metals which resist rusting and have high corrosion resistance such as the gold braze, the nickel braze and the like are used. Usable as solder are solder with Ag, solder with Cu, Au—Sn solder and the like, in addition to ordinary Pb—Sn solder. However, more preferred are solders such as Au—Sn solder and the like which resist rusting and have high corrosion resistances.

A joint made by means of molten glass is also a suitable airtight joint means, in addition to metal welding. Low melting-point powder glass and the like are exemplified as molten glass which can be filled and jointed airtightly. The joint between airtight partition materials can be filled with a low melting-point powder glass and the airtightness thereof can be secured by heating and melting. The low melting-point powder glass is brought to a glass state or crystallized. Further, as to ceramics other than glass, a ceramic joint agent is available which can be airtightly jointed by being baked.

That is, a joint means in which the main component of a joint is a metal, ceramics, glass or crystallized material, can be employed as the airtight joint means.

Note that when a joint is made by these airtight joint means, the temperature is increased to about 200° C.–400° C. in, for example, soldering to about 700° C.–1000° C. in brazing and to a metal melting temperature of about 1400° C. (for stainless steel) in the laser welding. Further, while low melting-point powder glass is used as the airtight joint molten glass, the melting point thereof is about 300° C.–600° C.

Note that the airtightness described in the present invention indicates the case in which the equivalent reference leak amount is $1 \times 10^{-9 Pa \cdot m^3/s}$, or less as a standard when measured by a helium leak detector shown in JIS Z2331 and the like (space volume in a test piece; 0.1–0.4 cm$^3$)

When the quivalent reference leak amount exceeds $1 \times 10^{-9 Pa \cdot 3/s}$, a high pressure/high temperature water vapor penetrates into the airtight partition members when they are subjected to autoclave sterilization and water vapor is accumulated when the autoclave sterilization is repeated. As a result, there is a possibility for dew to condense on the lens surface or for the lens to be frosted or for a coating and adhesive being applied to the lens surface, deteriorating the lends and rendering the observed image to be unacceptable.

Table 1 shows the relationship between the difference of equivalent reference leak amounts due to different joint methods and the presence of water vapor penetration.

It can be found that a permeable equivalent reference leak amount is different between the airtight structure made by welding, in other words, the airtight structure of the airtightly-sealed section shown in the embodiment and the watertight structure arranged by means of an ordinary O-ring and adhesive.

TABLE 1

| Joint Method | Equivalent reference leak amount (Pa · m$^3$/s) | Penetration of water vapor |
|---|---|---|
| Welding | $0.6 \times 10^{-10} - 1 \times 10^{-9}$ | No |
| Seal by O-ring (fluorine resin) | $1 \times 10^{-9} - 1 \times 10^{-8}$ | Yes |
| Seal by O-ring (silicone rubber) | $5 \times 10^{-8} - 5 \times 10^{-7}$ | Yes |
| Fixing by epoxy resin adhesive | $5 \times 10^{-10} - 1 \times 10^{-7}$ | Yes |

It can be found from the water vapor penetration data that when adhesion or sealing is made by means of polymeric material after autoclave sterilization, a water vapor penetrates through an adhered portion or a sealed portion, in contrast to a welded portion welded by brazing or fusion welding. This phenomenon becomes more remarkable when autoclave sterilization is performed repeatedly.

In the present invention, the eyepiece lens unit is airtightly sealed as described above. However, even if the eyepiece lens unit is not arranged as a perfectly airtight structure, the effect of the present invention can be obtained when, for example, it is sealed at a hermetic seal level higher than the watertight level of the shell of the endoscope.

In particular, when the eyepiece lens unit is thus arranged, a water absorbing material denoted by numeral 59 in FIG. 7 is disposed at, for example, the extreme end cover glass frame 35 in the eyepiece lens unit. With this arrangement, water vapor that has penetrated in a slight amount is absorbed by the water absorbing material 59. Thus, the problem with waterdrop deposits on a lens surface is prevented even if the autoclave sterilization is performed repeatedly. It is more effective to removably mount the water absorbing material 59 so that it can be replaced.

Note that even in the above arrangement, the joint of the eyepiece lens unit 33 and the partition members must be arranged to minimize the penetration of water vapor. For example, when the joint is to be sealed with an adhesive, an adhesive admitting less water vapor is to e used, e.g., epoxy adhesive, ceramic adhesive and the like rather than a silicone adhesive.

Further, when a polymeric material is used as the partition member of the eyepiece lens unit, super-engineering plastic, which is elaborate in the polymeric material, is used e.g. polyphenylene sulfide, polyether ketone, polyphenyl sulfon, and the like.

Further, a state near airtightness may be achieved by applying a gas barrier coating to the outer surface of the eyepiece lens unit. Finally, the eyepiece lens unit is sealed at a hermetic seal level at least higher than the watertight level of the shell of the endoscope.

Figure 8:
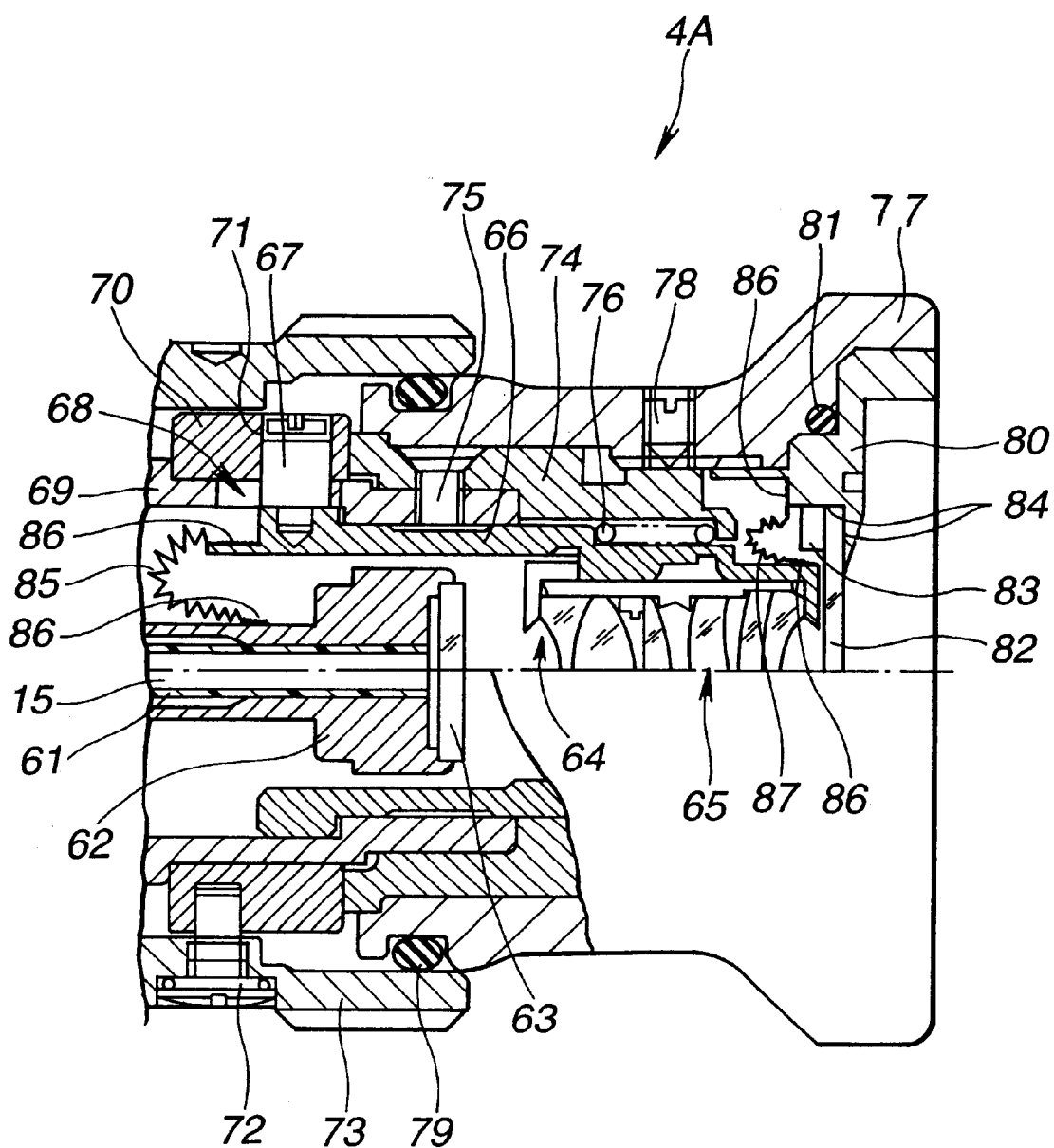
FIG. 8 is a view explaining another arrangement of the eyepiece section.

Note that while the bellows 40, whose diameter is substantially the same over the entire length thereof, is arranged as a tubular elastic airtight partition member, it may be arranged as a bellows whose diameter is not substantially the same as shown in FIG. 8.

As shown in the figure, for example, the image guide fiber 15 extends from an eyepiece section 4A together with a sheath tube 61 covering the image guide fiber 15.

The base end portion of the image guide fiber 15 is accommodated in an image guide frame 62 in the eyepiece section 4A. A sapphire cover glass 63 is airtightly jointed to the image guide frame 62 at a position where it covers the base end surface of the image guide fiber 15.

The image captured by the endoscope, which has passed through the cover glass 63, passes through an eyepiece lens unit 65, in which the eyepiece lens group 64 composed of a plurality of optical members is disposed, and observed by an observer.

The eyepiece lens unit 65 constitutes a movable optical system which permits visibility adjustment. A movable frame 66, which extends to cover the image guide frame 62, is disposed at the eyepiece lens unit 65. A first cam pin 67 is disposed to the outer periphery of the movable frame 66. The first cam pin 67 is engaged with a second cam groove 71, which is formed at an associating frame 70 obliquely with respect to a circumferential direction, through a support frame 69, at which a first cam groove 68 is formed, so that the first cam pin 67 moves linearly in parallel with the optical-axis. Note that a second cam pin 72 is disposed at the outer peripheral surface of the associating frame 70 so as to also engage with a visibility adjustment ring 73.

A fixed cylinder 74 is fixed to the support frame 69 on the eyepiece side thereof by a first screw 75. An elastic member 76 is interposed between the fixed cylinder 74 and the movable frame 66 to apply urging force in the optical-axis direction.

An eyepiece 77 is screwed with the fixed cylinder 74 and tightened and fixed by a looseness preventing screw 78. A first O-ring 79 is interposed between the eyepiece 77 and the visibility adjustment ring 73, and the visibility adjustment ring 73 is slidably arranged with respect to the eyepiece 77. The support frame 69 and the fixed cylinder 74 constitute a fixed frame together with an observation window fixing frame 80 and the image guide frame 62.

A second O-ring 81 is disposed to the inner peripheral surface of the eyepiece 77 on the eyepiece side thereof to achieve watertightness between it and the observation window fixing frame 80. The observation window fixing frame 80 is screwed with the eyepiece 77 and fixed thereto.

A cover glass 82, which has a diameter larger than that of the eyepiece lens unit 65, is sandwiched between the observation window fixing frame 80 and the a cover window presser 83 and jointed to the observation window fixing frame 80 by brazing the joint surfaces 84 therebetween.

A first bellows 85 acting as an expandable tubular airtight partition wall member, which is composed of metal or an elastic body such as resin, rubber or the like to which coating is applied, is airtightly jointed to the respective outer peripheral surfaces of the image guide frame 62 and the movable frame 66 through the airtight joints 86 formed at both the sides thereof.

In contrast, both the ends of a second bellows 87 are airtightly jointed on the respective stepless uniform surfaces of the movable frame 66 and the observation window fixing frame 80 through airtight joints 86 formed at both the sides of the second bellows 87.

The bellows 85 and 87 are bellows structural members expandable in the optical-axis direction and have a cylindrical surface or a flange surface for airtight joints. Otherwise, they are a tubular member having a diameter which changes over the entire length thereof.

As described above, the eyepiece lens unit 65, which is surrounded by the cover glass 63, the image guide frame 62, the first bellows 85, the movable frame 66, the second bellows 87, the observation window fixing frame 80 and the cover glass 82, is arranged as an airtightly-sealed section.

The operation of this endoscope of the embodiment is as follows.

When an operator looks through the cover glass 82 of the eyepiece section 4A or connects a video camera thereto, he or she rotates the visibility adjustment ring 73 to focus the image. Then, the associating frame 70 is rotated thereby in association with the second cam pin 72. The rotation of the associating frame 70 results in the linear movement of the movable frame 66 in the optical-axis direction through the second cam groove 71 of the associating frame 70, the first linearly-moving cam groove 68 of the support frame 69 and the first cam pin 67 engaged with both of them. When the movable frame 66 is thereby moved in the optical-axis direction, one or the other of the spaces between the movable frame 66 and the image guide frame 62 and the first bellows 85 is expanded by the contraction of the other space and vice versa as well as any one of the spaces between the movable frame 66 and the observation window fixing frame 80 and the second bellows 87 is expanded by the contraction of the other and vice versa. However, since both the ends of the first and second bellows 85 and 87 are both jointed through the airtightly-arranged ends thereof, the eyepiece lens unit 65 can be moved while maintaining an airtightly-sealed state as a whole.

The elastic member 76 prevents loose play of the eyepiece lens unit 65 by urging the movable frame 66 toward an objective side with respect to the fixed cylinder 74. However, when engagement play and the like are dimensionally suppressed, the elastic member 76 is not always necessary. Note that operation of the embodiment when it is subjected to autoclave sterilization is similar to that of the first embodiment.

The embodiment has the following effects.

Various types of airtightly-sealed eyepiece lens units can be arranged by using the bellows having a changing diameter as a tubular hard airtight partition member.

Another arrangement of an eyepiece lens unit 33A constituting an eyepiece section 4B will be described with reference to FIG. 9 and FIG. 10.

The eyepiece lens unit 33A of the embodiment is provided with only one eyepiece lens 91 in place of an eyepiece lens group 32 disposed to an eyepiece lens frame 39. The eyepiece lens 91 is made from glass or sapphire which is highly resistant against high pressure/high temperature water vapor, subjected to a metallizing treatment and directly jointed to the eyepiece lens frame 39 airtightly by soldering or the like. A volume change absorbing member 92 is disposed at the side peripheral surface of the eyepiece lens frame 39. Further, a water absorbing member 59 is disposed to an extreme end cover glass frame 35.

The volume change absorbing member 92 absorbs or provides a compensation effect for the volume change in an airtightly-sealed space. That is, it prevents the amount of rotating force of the visibility adjustment ring 34 from increasing or the visibility adjustment ring 34 having been rotated to be returned to its original position. These effects are caused by the gas in the eyepiece lens unit 33A being compressed when the bellows 40 is substantially deformed during the visibility adjustment and the volume in the airtightly-sealed eyepiece lens unit 33A being greatly changed thereby. In the described embodiment, the small-diameter bellows 93, is airtightly mounted.

More specifically, the internal space of the eyepiece lens unit 33A is airtightly sealed by an extreme end cover glass 36, the extreme end cover glass frame 35, the bellows 40, the eyepiece lens frame 39, the eyepiece lens 91 and the small-diameter bellows 93.

Figure 9:
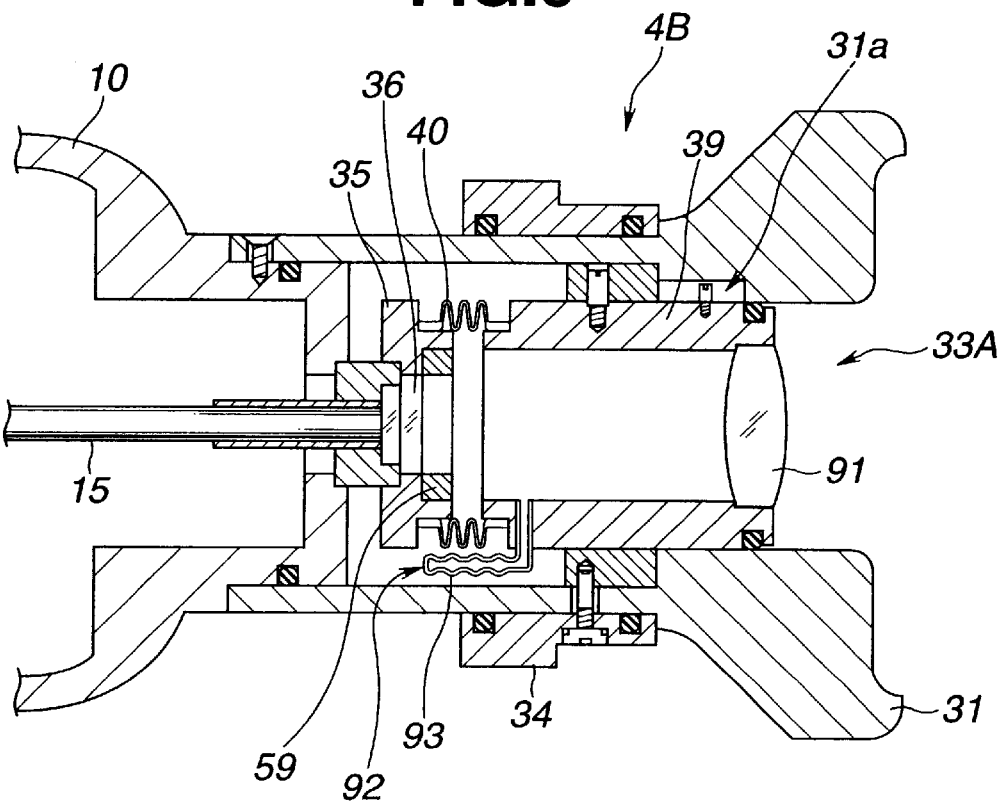
Figure 10A:
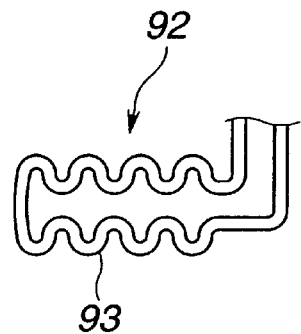
FIG. 10A is a view showing an ordinary state of a small diameter bellows.
Figure 10B:
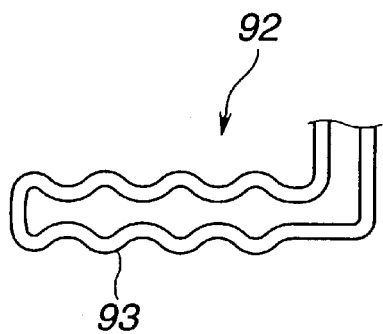
FIG. 10B is a view showing a state in which a volume change is adsorbed by the small diameter bellows.

The small-diameter bellows 93 acting as the volume change absorbing member 92 contracts as shown in FIG. 10A when the bellows 40 is expanded, whereas when the bellows 40 is contracted, the small-diameter bellows 93 is expanded as shown in FIG. 9 and FIG. 10B. That is, the volume change in the airtightly-sealed space, which is caused when the visibility adjustment is made, is absorbed by the expansion and contraction of the small-diameter bellows 93. Since the other arrangement of the embodiment is similar to that of the first embodiment, the same members are denoted by the same numerals and the description thereof is omitted.

When only a single eyepiece lens 91 is provided or when the eyepiece lens is not disposed in an airtightly-sealed space, that is, when the eyepiece lens acts as the optical window of an eyepiece lens unit, an effect similar to that of the first embodiment can be obtained by fabricating the air-tightly sealed partition member from an optical member which is resistant to the high pressure/high temperature water vapor used in the autoclave sterilization process.

In addition, in the embodiment, the water absorbing member is disposed in the airtightly-sealed space. Accordingly, even if the eyepiece lens unit is not arranged as a perfectly airtight structure and, for example, if it is partly bonded by an adhesive, an effect similar to that of the first embodiment is obtained. However, it is more preferable to arrange the eyepiece lens unit as a perfectly sealed airtight structure.

Figure 11:
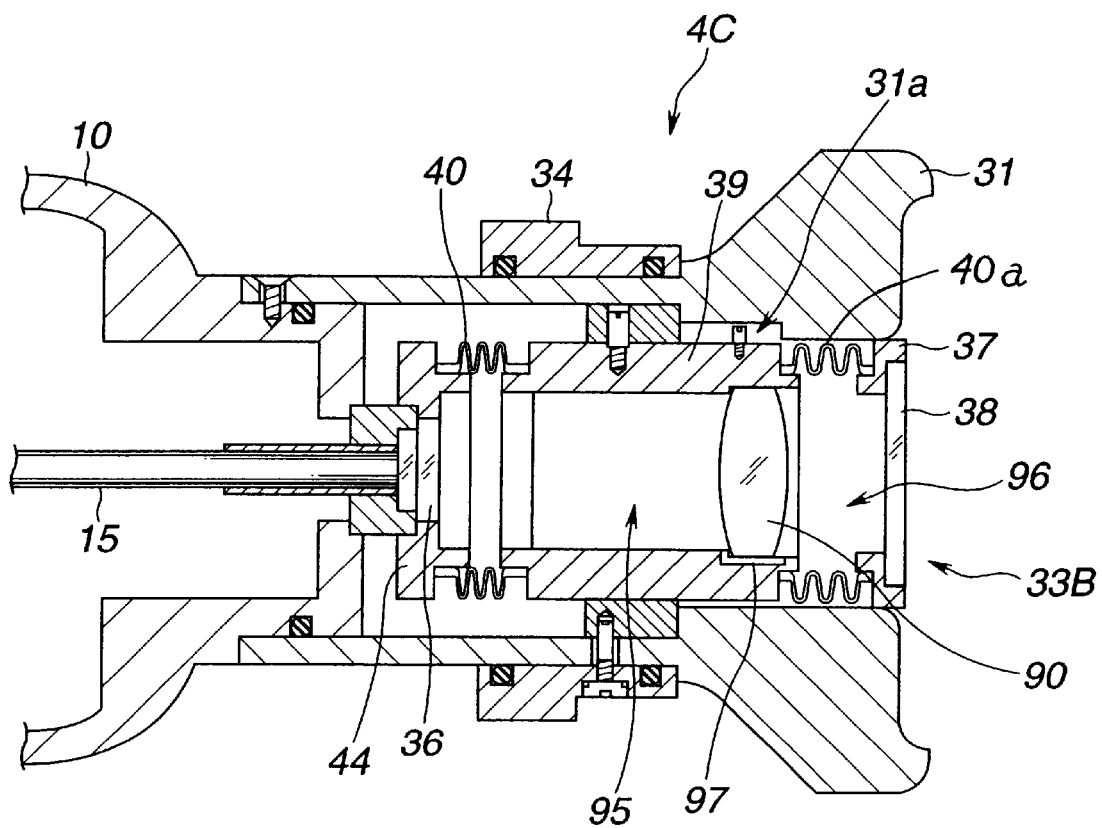
FIG. 11 is a view explaining still another arrangement of the eyepiece lens unit.

Another arrangement of an eyepiece lens unit 33B constituting an eyepiece section 4C is now described with reference to FIG. 11.

The eyepiece lens unit 33B of the embodiment includes bellows acting as a tubular elastic airtight partition members which are movable to two extreme positions, that is, to the extreme end side and the base end side of an eyepiece lens frame 39. More specifically, the eyepiece lens unit 33B includes a base end bellows 40a disposed to the base end side of the eyepiece lens frame 39, in addition to the above bellows 40.

The base end bellows 40a is airtightly jointed to the eyepiece lens frame 39 and to a base end cover glass frame 37. Thus, the internal space of the eyepiece lens unit 33B is airtightly bounded and sealed by an extreme end cover glass 36, an extreme end cover glass frame 35, the bellows 40, the eyepiece lens frame 39, the base end bellows 40a, the base end cover glass frame 37 and a base end cover glass 38.

In the embodiment, an eyepiece 31 is fixed to the base end cover glass frame 37 by an adhesive. When visibility is to be adjusted, only the eyepiece lens frame 39 is moved in the optical-axis direction. At the same time, if one of the bellows 40 and the base end bellows 40a is contracted, the other is extended.

Further, a ventilation hole 97 is formed at the surface where the eyepiece lens of the eyepiece lens frame 39 is jointed so as to communicate an eyepiece extreme end side space 95 with an eyepiece base end side space 96 which are arranged on opposite sides of the eyepiece lens 90. With this arrangement, when the gas in one of the airtight spaces is compressed in the visibility adjustment, the compressed gas is supplied to the other airtight space. The aforementioned problem that rotating the visibility adjustment ring 34 might cause the visibility adjustment ring 34 to be returned to its original position is now overcome.

Further, since the O-ring 54 shown in FIG. 3 is not used in the present embodiment, ring is more rotatable and possible the visibility adjustment deterioration of the O-ring is no longer a potential problem.

While the above embodiments have been described relative to a medical endoscope subjected to autoclave sterilization, the arrangement of the present invention is effectively generally usable to endoscopes subjected to water vapor sterilization, or those that are immersed in a fluid for a long time or exposed to water vapor as for example in highly humid environments encountered in some industrial applications.

Further, while the embodiments have been described as to the endoscope 1 having the soft insertion section 2 and the curved section 8 shown in FIG. 1, the arrangement of the present invention is also effective to endoscopes in which the portion thereof corresponding to the flexible tube 9 of the insertion section 2 is composed of a hard material.

Furthermore, the arrangement of the present invention is also effective to an endoscope whose insertion section 2 is flexible and which is not provided with the curved section 8.

That is, the arrangements of the embodiments are effective to all the endoscopes at least a portion of which are flexible.

In addition, the present invention is applicable to a hard endoscope using an image guide fiber as an image transmission means and having the insertion section 2 hard member over the entire length thereof. The invention can provide a hard endoscope whose assembling property and repairing property are better than those of the endoscope disclosed in DE19631840A1 as well as which can perform visibility adjustment, so that the operability of the visibility adjustment is greatly improved.

Note that breakage of the outer sheath tube of the curved section 8 may be prevented by permitting a check valve adapter 13A (FIG. 1) to be mounted on the ventilation mouthpiece 6b in place of the ventilation cap 13. The check valve adapter 13A functions so that when the pressure in the inner space of the endoscope 1 becomes higher than the external pressure by a predetermined pressure difference, the check valve opens to adjust or equalize the pressure in the inner space of the endoscope 1. In this case, no water vapor is positively driven to penetrate through a communicating portion, whereby deterioration of the inner parts of the endoscope is still prevented for a long time.

A second embodiment of the present invention will now be described with reference to FIGS. 12 and 13.

Figure 12:
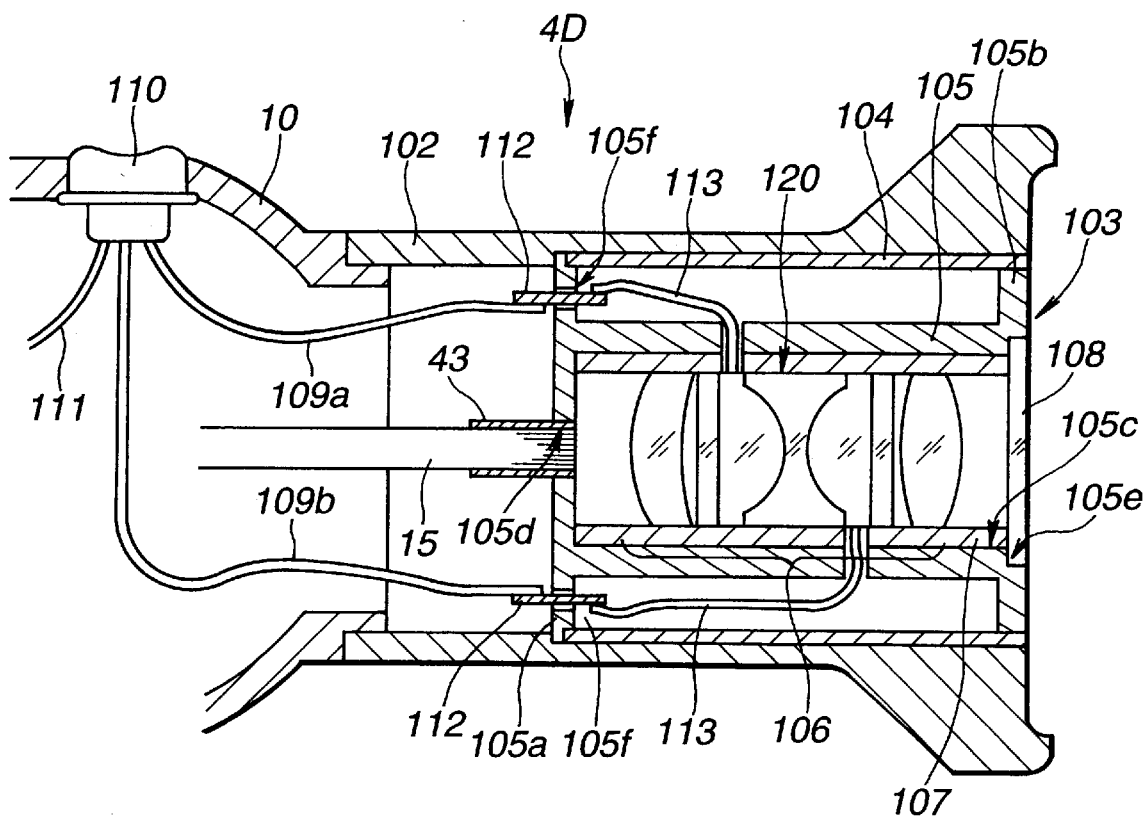
Figure 13:
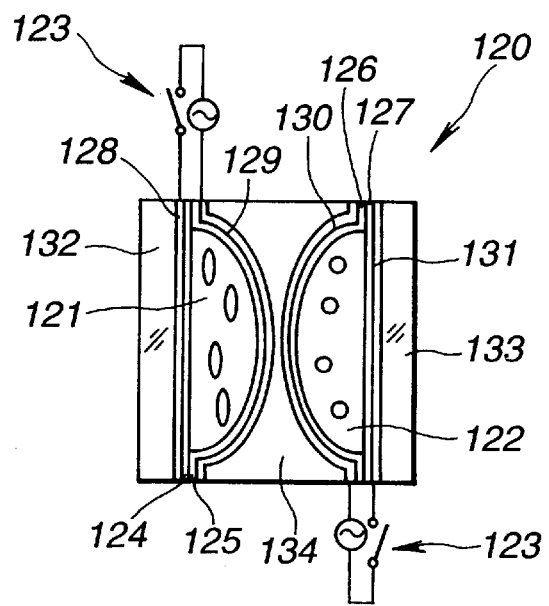

As shown in FIG. 12, an eyepiece section 4D of the embodiment has an eyepiece 102 integrally fixed to a main body 10. An eyepiece lens unit 103 having an eyepiece lens group 106 is disposed in the eyepiece 102.

The eyepiece lens unit 103 mainly comprises an outside frame 104 made of metal, a main body frame 105 made of metal, an eyepiece lens frame 107 made of metal, and a cover glass 108. The metal outside frame 104 is formed in an approximate pipe-shape and constitutes a shell; the metal main body frame 105 is formed to an approximate bobbin-shape, disposed to the internal peripheral surface of the outside frame 104, and has convex sections 105a and 105b formed at both sides thereof and an inner space 105C; the eyepiece lens frame 107 is disposed in the inner space 105c of the unit main body frame 105, formed as a pipe-shape and includes an eyepiece lens group 106 which is disposed in the inner hole thereof and has a plurality of optical lenses and a liquid crystal lens 120 acting as a focal position adjusting means which will be described later; and the cover glass 108 is mounted to the base ends of the eyepiece lens frame 107 and the main body frame 105 and made of sapphire.

A transparent hole 105d acting as an image guide fiber mounting section communicating with the inner space 105c is formed at the approximate center of the convex section 105a of the unit main body frame 105. A concave section 105e, in which the cover glass 108 is disposed, is disposed at the convex section 105b on the base end side thereof. Then, the length of the eyepiece lens frame 107 is formed shorter than the depth of the internal space 104c by the thickness of the cover glass 108.

In contrast, an image guide fiber 15 and signal cables 109a and 109b, which drive the liquid crystal lens 120 by transmitting electrical signals therethrough, are disposed in the interior of the main body 10. An end of the image guide fiber 15 is covered with a base end image guide fiber frame 43 made of metal. The base end image guide fiber frame 43 is jointed to the transparent hole 105d, and ends of the signal cables 109a and 109b are electrically connected to a contact terminal 112 fixed to the convex section 105a.

A visibility adjustment switch 110 is disposed to the signal cables 109a and 109b. The switch 110 can be operated from the outside of the main body 10. Further, a signal cable 111 extending from the switch 110 is electrically connected to an external device (not shown) or a battery disposed in the interior of an endoscope. The switch 110 is a push button type switch watertightly mounted on the main body 10 with its operating portion covered with rubber or the like. Thus, the switch 110 has very good operability.

An end of the outside frame 104 and the internal peripheral surfaces of the convex section 105a and the unit outside 104 are airtightly jointed to the outer peripheral surface of the convex section 105b by laser welding to thereby prevent the penetration of gas from the joint surface thereof. The respective optical lenses constituting the eyepiece lens group 106 are bonded and fixed to the internal peripheral surface of the eyepiece lens frame 107. Further, after a metallizing treatment is applied to the glass outer peripheral surface of the cover glass 108, the cover glass 108 is airtightly jointed to the internal peripheral surface of the concave section 105e of the main body frame 105 by brazing. With this arrangement, the penetration of gas through the joint surface of the cover glass 108 and the unit main body frame 105 is prevented.

In contrast, the end of the image guide fiber 15 is jointed to the base end image guide fiber frame 43 through, for example, molten glass which is filled between fiber wires, to the outer peripheral surface of the end of the fiber, and to the inner peripheral surface of the base end image guide fiber frame 43. With this arrangement, the penetration of gas through the joint surface between the fiber wires and the joint surface between the outer peripheral surface of the end of the fiber and the inner peripheral surface of the base end image guide fiber frame 43 is prevented.

The base end image guide fiber frame 43 is airtightly jointed to the transparent hole 105d of the convex section 105a by metal welding. As a result, the penetration of gas through the joint surface thereof is also prevented. Further, the contact terminal 112 is fixed to the convex section 105a integrally therewith by filling a through hole 105f formed at the convex section 105a with non-conductive molten glass. With this arrangement, the internal peripheral surface of the through hole 105f is insulated from the outer peripheral surface of the contact terminal 112 and the penetration of gas through the through hole 105f is prevented. The inner space of the eyepiece lens unit 103 is thus airtightly sealed.

An end of a relay cable 113 is connected to the liquid crystal lens 120 constituting the eyepiece lens group 106. The other end of the relay cable 113 is electrically connected to the contact terminal 112. With this arrangement, the liquid crystal lens 120, which is disposed in the airtightly sealed inner space of the eyepiece lens unit 103, is electrically connected to the external device (not shown) through the relay cable 113, the contact terminal 112 and the signal cables 109a and 109b. Thus, an electrical signal from the external device or the battery is transmitted to the liquid crystal lens 120 by the operation of the switch 110.

Note that airtight joints are obtained by using soldering, brazing, welding by laser or the like and hermetic sealing by molten glass and the like. Further, the relay cable 113 is connected to the liquid crystal lens 120 and the contact terminal 112 through the transparent holes formed at and communicating with the eyepiece lens frame 107 and the main body frame 105, respectively.

The liquid crystal lens 120 constituting the eyepiece lens group 106 will be described now with reference to FIG. 13. Note that the liquid crystal lens employed in the embodiment is a known liquid crystal lens disclosed in, for example, Japanese Unexamined Patent Publication No. 10-73758.

The illustrated liquid crystal lens 120 comprises a first liquid crystal main body 121, a second liquid crystal main body 122 and two pairs of electrodes 123. The first liquid crystal main body 121 is composed of a substantially transparent double refraction liquid crystal material; the second liquid crystal main body 122 is composed of a substantially transparent double refraction liquid crystal material similarly to the first liquid crystal main body 121; and the two pairs of electrodes 123 apply an electric field and a magnetic field to the first liquid crystal main body 121 and the second liquid crystal main body 122 as a whole. The liquid crystal lens 120 is arranged to change the focal point by making use of the difference between the double refraction of the first liquid crystal main body 121 and that of the second liquid crystal main body 122.

As a result, the refraction power of the liquid crystal is changed by the electrical signal transmitted to the liquid crystal lens 120 from the external device through the signal cables 109a and 109b when the switch 110 is operated. With this operation, the focal point of the liquid crystal lens 120 is changed, whereby visibility can be adjusted to suit an observer's vision.

In the above arrangement, liquid crystal layers constituting each of the liquid crystal main bodies 121 and 122 are formed by being overlapped in two layers so that the respective layers are oriented perpendicularly to each other, whereby a variable focus lens is realized without the need of a polarizer. Further, the liquid crystal main bodies 121 and 122 constituting the liquid crystal lens 120, orientation films 124, 125, 126 and 127, transparent electrodes 128, 129, 130 and 131, parallel flat lenses 132 and 133, and a concave lens 134 are composed of members selected from heat resistant members which can endure the autoclave sterilization temperatures. Further, nematic liquid crystal or the like is used as the liquid crystal.

As described above, the eyepiece lens group including the liquid crystal lens is disposed in the eyepiece lens unit which is arranged to prevent the penetration of gas thereinto through the joint surfaces. Accordingly, visibility adjustment can be carried out to suit an observer's vision by changing the lens focal length by changing the current to the liquid crystal lens. At the same time, a faulty field of vision due to an eyepiece lens frosted by a water vapor is prevented even if autoclave sterilization is performed.

Further, an effect similar to that of the first embodiment can be obtained while the electrical signal is needed. In addition, an eyepiece lens unit with a variable power mechanism can be constructed depending upon the liquid crystal optical system.

Note that the method of preventing the penetration of gas through the joint surfaces of the members constituting the eyepiece lens unit 103 is not limited to the arrangement of the present invention and may be arranged as described below.

For example, one or more of metal, ceramics, glass and sapphire are selected as the materials of the unit partition members. In contrast, one or more of welding using metal and joint using molten glass are selectively used as the joint means. The inner space is airtightly sealed by constituting it by the suitable combination the materials and the joint means.

Incidentally, a gas such as a water vapor and the like permeates plastic, rubber and elastomers such as thermoplastic elastomers and the like. Thus, it is impossible to obtain airtight seals by using these materials for the partition.

Further, a gas such as a water vapor and the like also permeates adhesives. Therefore, the use of adhesives in a joint makes airtight seals impossible. In particular, silicone rubber has very high water vapor permeability. Therefore, when a sealed space is formed by using the silicone rubber for the partition or, a silicone O-ring for a sealed portion, or a silicone adhesive for a joint, even if the sealed space is watertightly sealed, gas such as water vapor and the like is very likely to permeate the sealed space.

To cope with above problem, when an adhesive must be used, an adhesive such as an epoxy adhesive, a ceramics adhesive and the like is used, rather than a silicone adhesive.

Further, the application of gas barrier coating to the outer surface of the joint bonded by an adhesive is effective to obtain airtight sealing. When the coating is transparent, it is possible to apply the coating to the entire eyepiece lens unit. However, when the coating is not transparent, the coating task is carried out after the light transmissive element such as a glass cover and the like is masked so that the coating is not applied thereto.

Examples of the transparent coating are silica coating transformed from silazane and parylene resin coating. Examples of non-transparent coating is metal vapor deposition coating such as aluminum vapor deposition coating, solder dip coating and the like. Ceramic coating and the like are also effective as non-transparent coating in addition to the above. Examples of the solder are Sn solder, In—Sn solder, AS—Sn solder, Pd—Sn solder and the like.

Pre-arranging a water absorbing member in the interior of the eyepiece lens unit is effective to prevent the lens from becoming frosted. Note that the water absorbing member may be detachably disposed so that it can be replaced.

There is available a means for preventing the lens from becoming frosted by entirely filling the inner space of the eyepiece lens unit with a transparent filler such as silicone oil or the like.

An arrangement of an eyepiece lens unit 103A with a variable focus lens which constitutes an eyepiece section 4E will now be described with reference to FIG. 14 and FIG. 15.

Figure 14:
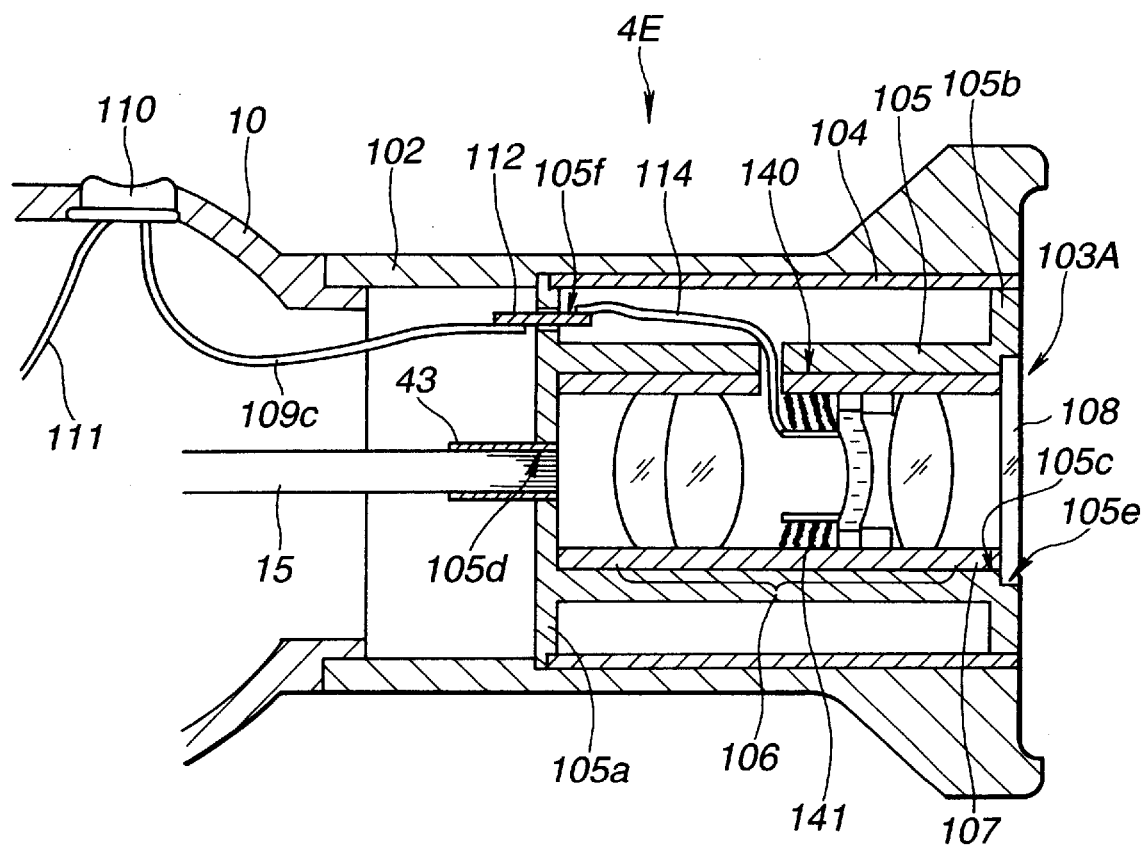

As shown in FIG. 14, in the embodiment, the eyepiece lens unit 103A comprises a variable focus lens 140 and a actuator section 141 in place of the liquid crystal lens 120 which is disposed in the eyepiece lens group 106 constituting the eyepiece lens unit 103 of the second embodiment. The variable focus lens 140 constitutes a focus position variable means and is composed of a transparent fluid; and the actuator section 141 deforms the variable focus lens 140.

An end of a relay cable 114 is connected to the actuator section 141. The other end of the relay cable 114 is connected to a contact terminal 112 through transparent holes which are formed in an eyepiece lens frame 107 and a main body frame 105 and communicated with each other.

With this arrangement, an electrical signal from an external signal cable 109c is transmitted to the variable focus lens 140 of the airtightly-sealed eyepiece lens unit 103. The other arrangement of the embodiment is similar to that of the second embodiment and the same components are denoted by the same numerals and the description thereof is omitted.

Figure 15A:
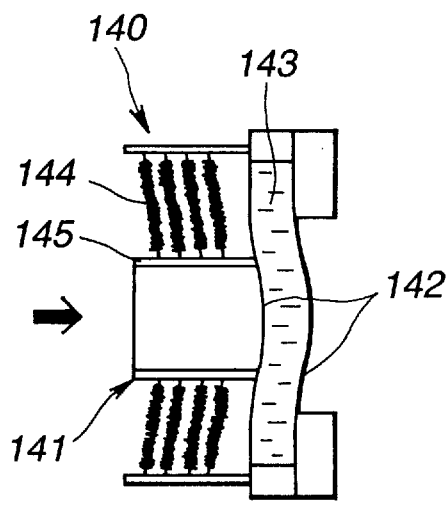
Figure 15B:
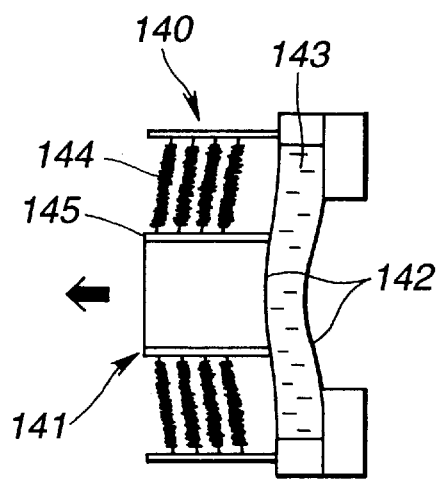

As shown in FIGS. 15A and 15B, the variable focus lens 140 mainly comprises a pair of heat resistant transparent elastic films 142 and a transparent actuation fluid 143 filling the space between the pair of transparent elastic films 142.

The actuator section 141 comprises a pressurizing drive section 144 and a shaft section 145. The pressurizing drive section 144 is composed of a piezoelectric device; and the shaft section 145 is fixed to the pressurizing drive section 144 and pushes and pulls the transparent elastic films 142 as the pressurizing drive section 144 is moved.

As a result, an electrical signal is transmitted to the actuator section 141 from the external signal cable 109c of the eyepiece lens unit 103A by operating the switch 110 as shown in FIGS. 15A and 15B. The shaft section 145 is moved as shown by an arrow to thereby change the shape of the variable focus lens 140 so as to change the focal point. With this arrangement, visibility can be adjusted to suit an observer's vision.

As described above, the shape of the variable focus lens is changed by moving the actuator section forward and rearward by flowing the current thereto, whereby a focal length is changed so as to adjust the visibility in accordance with the observer's vision. The other operation and effects of the embodiment are similar to those of the aforesaid embodiment.

Figure 16:
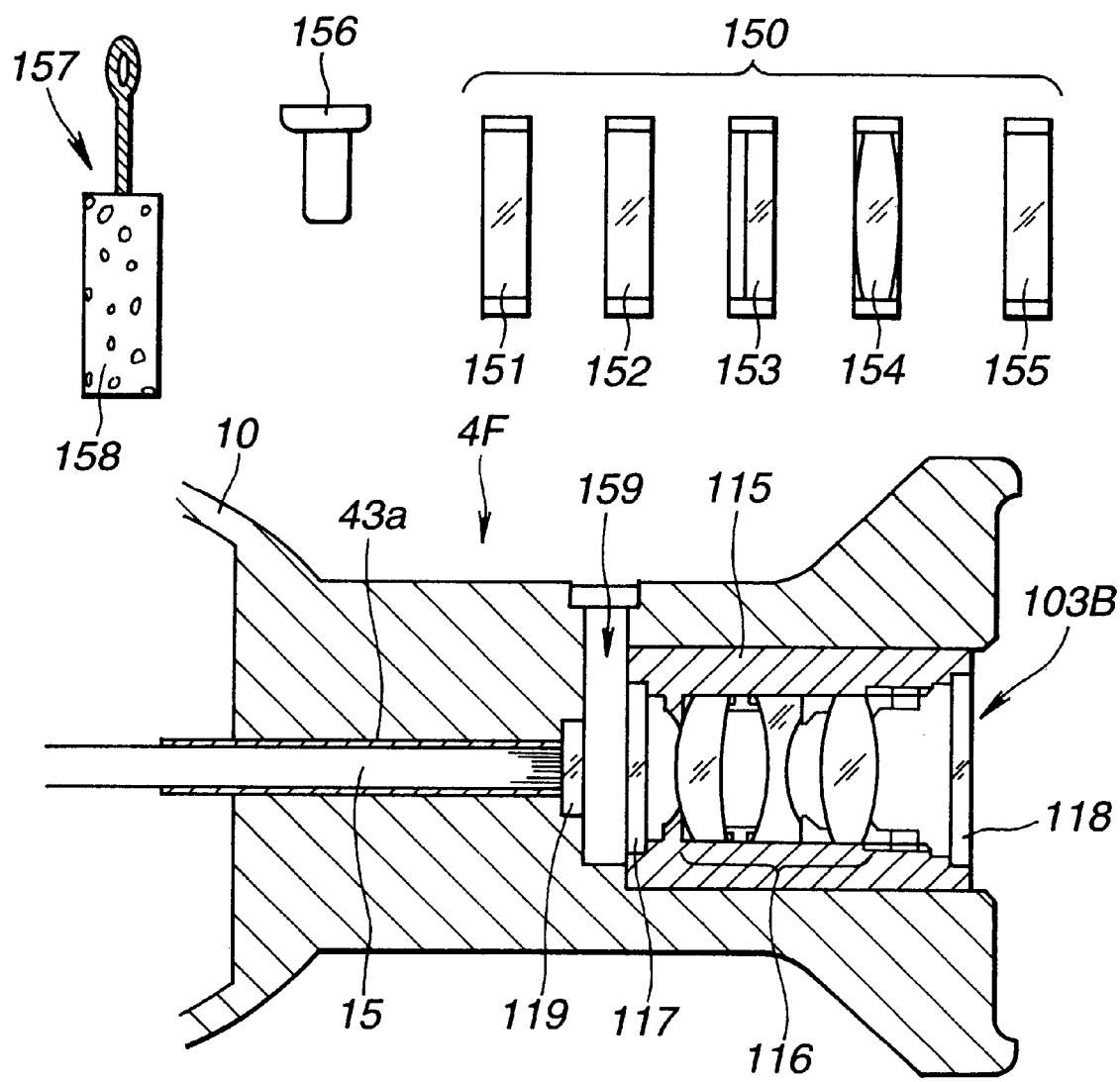
FIG. 16 is a view explaining another arrangement of a eyepiece section according to a third embodiment of the present invention.

A third embodiment of the present invention will now be described with reference to FIG. 16.

In an eyepiece section 4F of the embodiment, a visibility adjustment member mounting section 159 (hereinafter, referred to as the "member mounting section") is disposed in an image transmission light passage between an end of an image guide fiber 15 and an eyepiece lens unit 103B. The member mounting section 159 acts as an air-converted light passage length changing member mounting section into which a visibility adjustment member 150 is inserted. The visibility adjustment member 150 acts as an air-converted light passage length changing member for converting an air-converted light passage length. That is, the visibility adjustment member 150 acts as a focal position varying means. As described below, a plurality of different kinds of visibility adjustment members 150 are prepared. Note that numeral 156 denotes a rubber lid which is mounted on the member mounting section 159 after the visibility adjustment member 150 is disposed in the member mounting section 159 in order to prevent the removal of the visibility adjustment member 150.

A plurality of visibility adjustment members 150 are prepared such as, for example, a first member 151, a second member 152, . . . , a fifth member 155 and they can be selectively disposed in the member mounting section 159.

In the visibility adjustment members 150, the first member 151 and the second member 152 are composed as, for example, an optical member having a different refraction, and the third member 153 is composed of an optical member having a different thickness. The visibility adjustment members 150 change the air-converted light passage length between the end of the image guide fiber 15 and the eyepiece lens unit 103B from the above difference.

The fourth member 154 is composed as a lens-shaped focal length changing optical member. The fifth member 155 is a visibility adjustment member for connecting a camera head acting as an image input device having a CCD. The fifth member 155 is composed of, for example, quartz or sapphire which is an optical member having double refractivity. The fifth member 155 adjusts the focus between the CCD and the end surface of the image guide fiber as well as acts as a low-pass filter for removing moire interference fringes.

The eyepiece lens unit 103B comprises a metal eyepiece lens frame 115, an eyepiece lens group 116 and cover glasses 117 and 118. The eyepiece lens group 116 is disposed in the eyepiece lens frame 115 and composed of a plurality of optical lenses; and the cover glasses 117 and 118 are mounted to both ends of the eyepiece lens frame 115 and each of them is composed of high temperature resistant glass such as sapphire or the like.

Then, the cover glasses 117 and 118 are subjected to a metallizing treatment on the outer peripheral surfaces thereof and jointed by brazing to the inner peripheral surface of the extreme end of the eyepiece lens frame 115 and to the inner peripheral surface of the base end thereof, respectively.

In contrast, a fiber cover glass 119, which is composed of high temperature resistant glass such as sapphire or the like, is airtightly jointed to a main body 10 at the end surface of the image guide fiber 15 on the endoscope side. With this arrangement, no water vapor penetrates into the end of the image guide fiber 15.

Note that the respective airtight joints are jointed by any of soldering, brazing, welding using laser or the like, or molten glass sealing and the like. Further, a waterdrop wiping brush 157 is provided to remove waterdrops deposited on the surface of the cover glass 117 or on the surface of the fiber cover glass 119. A high water absorbing member such as a sponge 158 or the like is located at the extreme end of the brush 157. Numeral 43a denotes a metal image guide fiber frame for covering the end of the image guide fiber 15. While the eyepiece lens unit 103B is integrally fixed to the eyepiece section 4F integrally in the present embodiment, the eyepiece lens unit 103B may be detachably disposed to the eyepiece section 4F. With this arrangement, the waterdrop deposited on the eyepiece section cover glass 117 and on the fiber cover glass 119 can be easily wiped off.

As described above, when a desired visibility adjustment member is selected from the plurality of visibility adjustment members and disposed in the member mounting section, the air-converted light passage length between the end surface of the image guide fiber and the eyepiece lens unit can be changed, that is, visibility can be adjusted in accordance with the vision of an observer by changing the focus point of an eyepiece lens.

When the fifth member for connecting the camera head is disposed in the member mounting section, the CCD of the camera head can be focused on the end surface of the image guide fiber. In addition, the optical image transmitted from the image guide fiber causes double refraction through the double refractive optical member, whereby the occurrence of moire due to the meshes of a fiber can be suppressed.

Further, the lens-shaped focal length changing optical member as the fourth member, which is disposed in the member mounting section, can not only adjust visibility but also change the magnification of the eyepiece lens.

In addition, while waterdrops deposits on the cover glass when autoclave sterilization is performed, it can be wiped off with the waterdrop wiping brush. At the time, waterdrops or vapor cannot deposit in the interior of the eyepiece lens unit and on the end surface of the image guide fiber.

Figure 17:
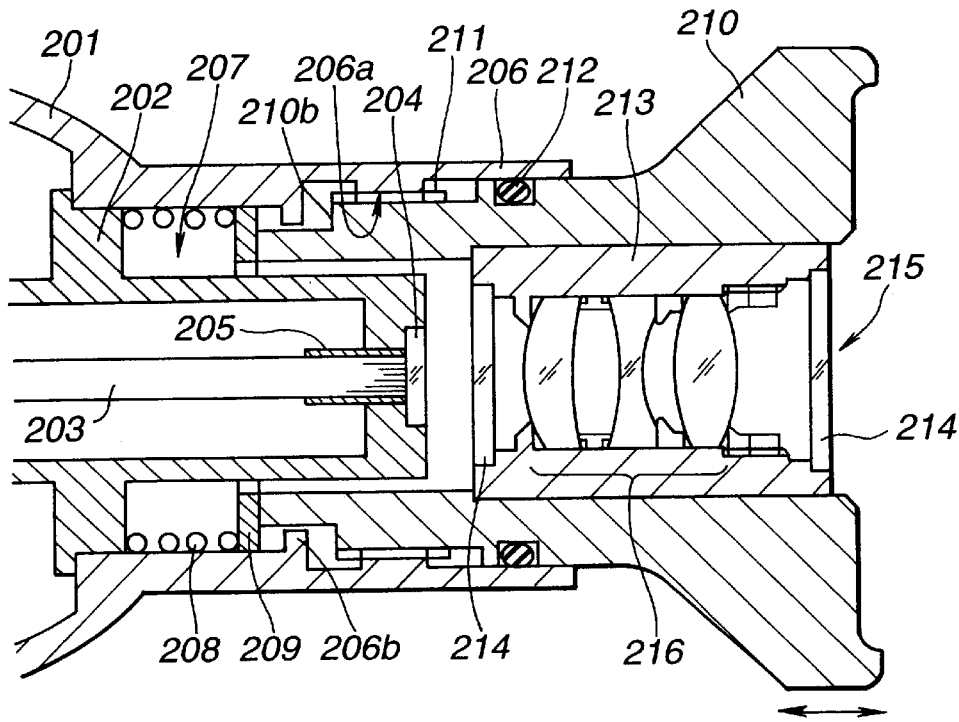
FIG. 17 is a sectional view explaining still another arrangement of the eyepiece section of the endoscope main body according to a fourth embodiment of the present invention.

A fourth embodiment of the present invention will now be described with reference to FIG. 17.

The embodiment is arranged such that an eyepiece frame 210 is detachably mounted on the main body 201 of an endoscope 1.

As shown in the figure, an image guide fiber frame 202 (hereinafter, abbreviated as fibre guide) having a transparent hole is fixed to the base end of the main body 201. A metal mouthpiece 205 for covering an image guide fiber 203 is airtightly jointed to the transparent hole of the fiber frame 202 by metal welding such as brazing or the like. A sapphire cover glass 204 is airtightly jointed to the base end of the fiber frame 202. Note that the metal mouthpiece 205 is airtightly jointed to an end of the image guide fiber 203 by molten glass.

An eyepiece fixing section 206, which projects in a cylindrical shape coaxially with the fiber frame 202 and has a female screw 206a formed at the inner peripheral surface thereof, is mounted to the base end of the main body 201. A coil spring 208 is disposed in the interval section 207 between the inner peripheral surface of the eyepiece fixing section 206 and the fiber frame 202. A washer 209 is disposed on the coil spring 208 on the base end surface side thereof. Note that numeral 206b denotes a stopper peripherally projecting from the inner peripheral surface of the main body 201. The stopper 206b prevents the removal of the coil spring 208 from the interval section 207.

Further, a male screw 211 which is screwed into the female screw 206a is formed at the outer peripheral surface of the eyepiece frame 210 at the extreme end thereof. When the female screw 206a is screwed on the male screw 211, the extreme end surface of the eyepiece frame abuts against the washer 209.

A peripheral concave portion is formed at the eyepiece frame 210 at substantially the center thereof. An O-ring 212 is disposed in the concave portion to obtain water tightness between the inner peripheral surface of the eyepiece fixing section 206 and the outer peripheral surface of the eyepiece frame 210 as well as to apply rotational resistance between the eyepiece frame 210 and the eyepiece fixing section 206.

A lens frame 213, which has an eyepiece lens group 216 composed of a plurality of optical lenses and disposed in the inner hole of the lens frame 213, is disposed on the eyepiece frame 210. An eyepiece lens unit 215 is arranged by airtightly jointing a sapphire cover glasses 214 to the extreme end and the base end of the lens frame 213.

The operation of the endoscope arranged as described above will now be described.

When the endoscope is used, the male screw 211 of the eyepiece frame 210 is screwed into the female screw 206a of the eyepiece fixing section 206 to thereby mount the eyepiece frame 210 on the main body 201. At the same time, the coil spring 208 urges the extreme end surface of the eyepiece frame 210 through the washer 209. Then, the eyepiece frame 210 is integrally fixed to and held by the eyepiece fixing section 206 therewith at a desired position by the contact resistance produced by the urging force to the portion where the female screw 206a is screwed on the male screw 211 and by the contact resistance produced thereby to the inner peripheral surface of the eyepiece fixing section 206 of the O-ring 212. Note that a means for fixing the eyepiece section to the main body 201 may be other than the above arrangement and may be provided, for example, separately.

The eyepiece frame 210 can be moved in the direction in which it is tightened until the end surface 210b thereof abuts against the stopper 206b. The movement of the eyepiece frame 210 in the optical-axis direction changes the distance between the base end surface of the image guide fiber 203 and the eyepiece lens group 216 so as to adjust the focus point. That is, the focus position changing means of the embodiment is the position changing means which can fixedly dispose the eyepiece section having the eyepiece lens unit detachable to the main body at a desired position.

The endoscope can be rinsed after it is used in a state when the eyepiece frame 210 is integrated with the main body 201. However, when the endoscope is sterilized in the autoclave apparatus, the eyepiece frame 210 and the main body 201 are separately sterilized.

Further, the eyepiece frame 210 and the main body 201 may be sterilized in the autoclave apparatus in an assembled state. In this case, however, there is a possibility for water vapor to penetrate into the space formed between the eyepiece frame 210 and the main body 201 deteriorating vision by dew condensed on the surfaces of the cover glasses 204 and 214. To cope with this problem, the eyepiece frame 210 is separated from the main body 201 after sterilization and the surfaces on which the dew now condensed are cleaned.

As described above, since the eyepiece frame and the main body are arranged separately so as to be detachable from each other, the components constituting the endoscope need not be jointed to each other airtightly as a whole. As a result, there can be provided an endoscope which can be subjected to autoclave sterilization while reducing the manufacturing cost thereof. The other operation and effects of the present embodiment are similar to those of the aforesaid embodiments.

Figure 18:
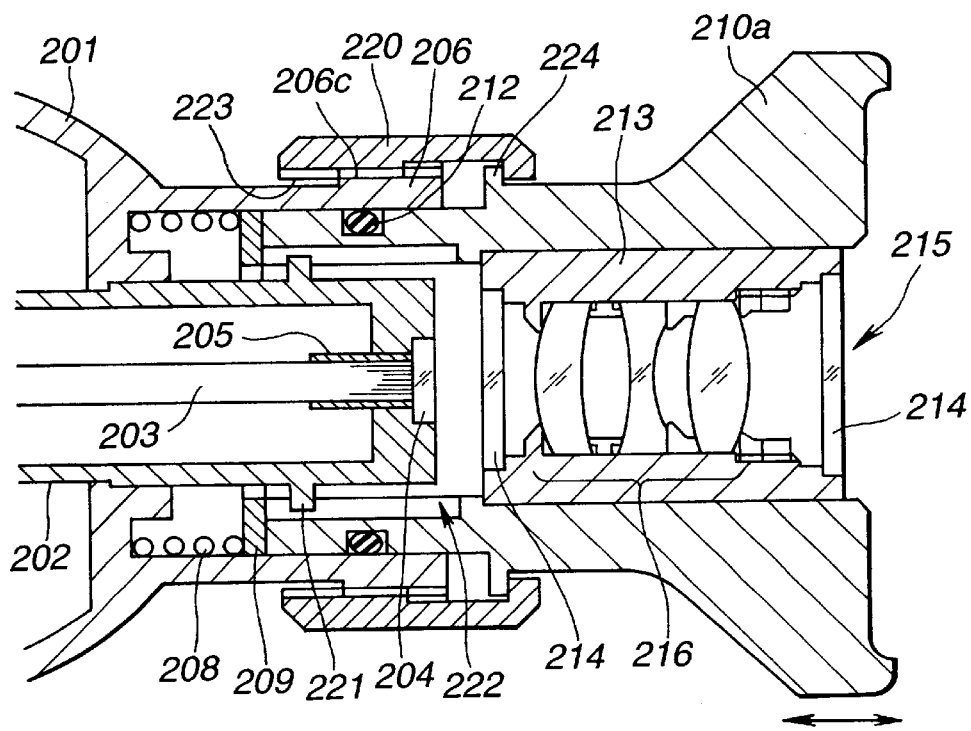
FIG. 18 is a sectional view explaining a fifth embodiment of the present invention.

A fifth embodiment of the present invention will now be described with reference to FIG. 18.

In the embodiment, an eyepiece frame 210a is detachably arranged with respect to a main body 201 and fixed thereto by a fixing ring 220.

As shown in the figure, a male screw 206c is formed at the outer peripheral surface of an eyepiece fixing section 206 on the base end side thereof. Further, two convex sections 221, which project externally, are disposed to the outer periphery of an image guide fiber frame 202 fixed to the base end of the main body 201 at symmetrical positions thereof.

In contrast, the eyepiece frame 210a of the embodiment is disposed with its extreme end slidably inserted into the inner peripheral surface of the eyepiece fixing section 206. The engagement of these two components prevents dislocation and inclination of the image guide fiber 203 with respect to the eyepiece lens group 216 in an axial direction. The eyepiece frame 210a has a groove 222 formed at the inner peripheral surface thereof in the optical-axis direction to permit the convex sections 221 to be disposed therein. The insertion of the convex sections 221 into the groove 222 prevents dislocation and inclination of the eyepiece frame 210a with respect to the main body 201 in the axial direction.

Further, a peripheral groove is formed at the outer peripheral surface of the eyepiece frame 210a at the extreme end side thereof. A watertight O-ring 212 is disposed in the peripheral groove so as to come into intimate contact with the inner peripheral surface of the eyepiece fixing section 206. The fixing ring 220 is rotatably disposed on the outer peripheral surface of the eyepiece frame 210a at the center thereof. The fixing ring 220 has a female screw 223 formed thereat which is screwed on the male screw 206c of the eyepiece fixing section 206.

Note that the extreme end surface of the eyepiece frame 210a abuts against a washer 209. Numeral 224 denotes a locking convex section acting as a stopper. The locking convex section 224 prevents the removal of the fixing ring 220 from the eyepiece frame 210a and locates the eyepiece frame 210a at a desired position. The other arrangement of the embodiment is similar to that of the fourth embodiment, and the same components are denoted by the same numerals and the description thereof is omitted.

The operation of the endoscope arranged as described above will now be described.

When the endoscope is used, the eyepiece frame eyepiece frame 210a is mounted on the main body 201. At the time, the female screw 223 of the fixing ring 220 is screwed on the male screw 206c. Then, the locking convex section 224 presses the fixing ring 220. As a result, the extreme end surface of the eyepiece frame 210a abuts against the washer 209 so that a coil spring 208 pushes the eyepiece frame 210a toward a base end side. With this operation, a contact resistance is applied to the portion where the female screw 223 is screwed on the male screw 206c so that the eyepiece frame 210a is fixed to and held by the eyepiece fixing section 206 integrally therewith.

In this state, the fixing ring 220 is rotated in a direction in which it is tightened, whereby the eyepiece frame 210a is moved toward the main body 201. Since the convex sections 221 are inserted into the groove 222 at the time, the eyepiece frame 210a smoothly moves in the optical-axis direction without being rotated by the rotary torque applied thereto. With this operation, the focus point is adjusted by changing the distance between the base end surface of the image guide fiber 203 and the eyepiece lens group 216.

After the endoscope is used, it is sterilized in the autoclave apparatus by separating the eyepiece frame 210a from the main body 201 by rotating the fixing ring 220.

As described above, when the eyepiece frame is to be connected to the main body through the fixing ring, it can be so connected solely by moving in the optical-axis direction without being rotated with respect to the main body. With this arrangement, even if a camera such as a CCD is connected to the eyepiece frame, the focus point can be adjusted in a state it is connected thereto. The engagement of the eyepiece frame 210a with the eyepiece fixing section 206 prevents dislocation and inclination of the image guide fiber 203 with respect to the eyepiece lens group 216 in the axial direction. The other operation and effect of the embodiment are similar to those to the fourth embodiment.

The present invention is by no means limited to the above embodiments and it goes without saying that various improvements can be made without departing from the spirit and scope of the present invention.

What is claimed is:

1. An endoscope suitable for autoclave sterilization comprising:
    an insertion section having a surrounding, watertightly sealed protective shell, an objective lens section being disposed at one extreme end of the insertion section for focusing a subject image;
    an eyepiece section located on a base end of said endoscope and including at least an eyepiece lens;
    an image guide fiber disposed in said insertion section and composed of an optical fiber bundle for transmitting the subject image focused by the objective lens section;
    an eyepiece lens unit disposed in said eyepiece section, in a manner that causes the eyepiece lens to confront a base end surface of said image guide fiber and provides a hermetic seal level at least as high as the watertight seal level of the protective shell of the endoscope; and
    a focus position changing structure at said eyepiece section which allows changing the focus of the eyepiece lens;
    wherein a soft section acting as the protective shell of the insertion section formed using a flexible polymeric material is provided to at least a portion of the insertion section, and the protective shell at the soft section is formed with a watertight seal level for preventing the penetration of the liquid in using the endoscope into the interior thereof but permitting the penetration of the high pressure/high temperature water vapor in autoclave sterilization into an interior thereof, and
    wherein said eyepiece lens unit is sufficiently pressure resistant to prevent the breakage thereof caused by negative pressure and positive pressure encountered in autoclave sterilization and has a hermetic seal level that prevents the penetration of high pressure/high temperature water vapor during autoclave sterilization into an interior thereof.

2. An endoscope suitable for autoclave sterilization according to claim 1, wherein said eyepiece lens unit comprises a plurality of airtight partition members and an airtight joint which airtightly joins the airtight partition members to each other so that the interior of said eyepiece lens unit is hermetically sealed at an airtight seal level higher than the watertight seal level of the shell of the endoscope.

3. An endoscope suitable for autoclave sterilization according to claim 2, wherein the airtight partition members are formed of a material selected from the group consisting of: metal, ceramics, glass and crystalline material and said airtight joint is a joint made by using metal welding such as fusion welding, pressure welding, brazing or soldering or using molten glass.

4. An endoscope suitable for autoclave sterilization according to claim 2, further including a water absorbing member disposed in an inner space of said eyepiece lens unit.

5. An endoscope suitable for autoclave sterilization according to claim 1, wherein said focus position changing structure has a member for hermetically sealing, said eyepiece section at a level higher than the watertight seal level of the protective shell and wherein said eyepiece lens unit is held to be movable in the optical-axis direction of the eyepiece section.

6. An endoscope suitable for autoclave sterilization according to claim 1, wherein said focus position changing structure is a tubular elastic airtight partition member which constitutes said eyepiece lens unit and can expand and contract in an optical-axis direction.

7. An endoscope suitable for autoclave sterilization according to claim 6, wherein the tubular elastic airtight partition member is composed of a thin metal sheet formed as a bellows structure.

8. An endoscope suitable for autoclave sterilization according to claim 6, wherein the tubular elastic airtight partition member is airtightly jointed to an eyepiece lens frame for holding and fixing the eyepiece lens by an airtight joint, whereby when a focus point is to be adjusted, the tubular elastic airtight partition member expands and contracts while maintaining the airtightness in said eyepiece lens unit so as to move forward and rearward in the optical-axis direction of the eyepiece lens.

9. An endoscope suitable for autoclave sterilization according to claim 6, wherein said eyepiece lens unit further comprises a volume change absorbing member airtightly jointed thereto which compensates for a change in the inner space of said eyepiece lens unit caused by expansion and contraction of the tubular elastic airtight partition member.

10. An endoscope suitable for autoclave sterilization according to claim 6, including two tubular elastic airtight partition members in said eyepiece lens unit on opposed sides of said eyepiece lens, and a ventilation hole formed to communicate spaces defined on the opposed sides of the eyepiece lens so as to compensate for volume changes of the spaces.

11. An endoscope suitable for autoclave sterilization according to claim 1, wherein said focus position changing structure is a variable focus lens disposed in said eyepiece lens unit.

12. An endoscope suitable for autoclave sterilization according to claim 11, wherein the variable focus lens is a liquid crystal.

13. An endoscope suitable for autoclave sterilization according to claim 1, wherein said focus position changing structure is an air-converted light passage length changing member which is selectively disposed in an image transmission light passage located at a position nearer to a base end side than the base end surface of said image guide fiber acting as the image projecting end thereof.

14. An endoscope suitable for autoclave sterilization according to claim 13, wherein the air-converted light passage length changing member includes a plurality of selectable optical members each having respective and different thickness and refraction characteristics and each being selectively placeable in the air-converted light passage length changing member mounting section.

15. An endoscope suitable for autoclave sterilization according to claim 14, wherein the air-converted light passage length changing member mounting section is formed in the image transmission light passage between the base and surface of said image guide fiber and said airtightly sealed eyepiece lens unit.

16. An endoscope suitable for autoclave sterilization according to claim 1, wherein said focus position changing structure is a position fixing structure that enables said eyepiece section to be fixedly and detachably mounted at a desired, adjustable position along an optical-axis direction relative to a main body portion of the endoscope.

17. An endoscope suitable for autoclave sterilization according to claim 16, wherein the position fixing structure has a locking section and a presser section mounted to said eyepiece section and the eyepiece section mounting section of the main body.

18. An endoscope suitable for autoclave sterilization according to claim 1, wherein a seal member is further interposed between said eyepiece section and the eyepiece section mounting section.

19. An endoscope suitable for autoclave sterilization according to claim 1, wherein a space into which high pressure/high temperature water vapor penetrates during autoclave sterilization is eliminated from the light passage from the base end surface of said image guide fiber acting as the image projecting end thereof to the base end side optical window of said eyepiece lens unit exposed to the shell of the endoscope.

20. An endoscope suitable for autoclave sterilization according to claim 19, wherein said eyepiece lens unit includes two optical windows, including an extreme end side optical window and a base end side optical window, the extreme end side optical window of said eyepiece lens unit is disposed at the image projecting end surface of said image guide fiber in intimate contact therewith and the base end side optical window thereof is disposed so as to expose from the shell of the endoscope.

21. An endoscope suitable for autoclave sterilization according to claim 1, wherein said focus changing structure further comprises a visibility adjustment unit operable by an operator and arranged separately from elements constituting said airtight eyepiece lens unit.

22. An endoscope suitable for autoclave sterilization according to claim 21, wherein the visibility adjustment unit is watertightly formed relative to the shell of the endoscope.

23. An endoscope suitable for autoclave sterilization, the endoscope comprising:
   an insertion section having an objective lens section disposed at one end of the insertion section for focusing a subject image;
   an image guiding fiber, disposed in said inserting section and having first and second ends, the first end being mounted adjacent said objective lens section for receiving said subject image;
   an eyepiece section located adjacent the second end of the image guiding fiber in a position to view the subject image provided via the image guiding fiber; and
   a sealing section disposed about the second end of the image guiding fiber and the eyepiece section and so formed as to prevent penetration of water vapor into spaces defined between and about the eyepiece section and the second end of the image guiding fiber when the endoscope is subjected to the autoclave sterilization, the endoscope further including a focusing structure that enables changing a relative distance between the eyepiece section and the second end of the image guiding fiber, in which the sealing section comprises a bellows and the focusing structure comprises a ring that enables changing the position of the eyepiece section relative to the second end of the image guiding fiber.

24. The endoscope of claim 23, in which the bellows are comprised of at least two sections disposed on opposed sides of the eyepiece section.

25. An endoscope suitable for autoclave sterilization, the endoscope comprising:
    an insertion section having an objective lens section disposed at one end of the insertion section for focusing a subject image;
    an image guiding fiber, disposed in said inserting section and having first and second ends, the first end being mounted adjacent said objective lens section for receiving said subject image;
    an eyepiece section located adjacent the second end of the image guiding fiber in a position to view the subject image provided via the image guiding fiber; and
    a sealing section disposed about the second end of the image guiding fiber and the eyepiece section and so formed as to prevent penetration of water vapor into spaces defined between and about the eyepiece section and the second end of the image guiding fiber when the endoscope is subjected to the autoclave sterilization, the endoscope further including a focusing structure that enables changing a relative distance between the eyepiece section and the second end of the image guiding fiber, in which the focusing structure includes elements which have the effect of maintaining the overall volume of free space bounded by the sealing section substantially constant, as the position of the eyepiece section is moved relative to the second end of the image guiding fiber, the endoscope further comprising a water absorbing material located adjacent the free spaces.

26. An endoscope suitable for autoclave sterilization, the endoscope comprising:
    an insertion section having an objective lens section disposed at one end of the insertion section for focusing a subject image;
    an image guiding fiber, disposed in said inserting section and having first and second ends, the first end being mounted adjacent said objective lens section for receiving said subject image;
    an eyepiece section located adjacent the second end of the image guiding fiber in a position to view the subject image provided via the image guiding fiber; and
    a sealing section disposed about the second end of the image guiding fiber and the eyepiece section and so formed as to prevent penetration of water vapor into spaces defined between and about the eyepiece section and the second end of the image guiding fiber when the endoscope is subjected to the autoclave sterilization, the endoscope further including a focusing structure that enables changing a relative distance between the eyepiece section and the second end of the image guiding fiber, in which the focusing structure comprises an electrically adjustable and focusable lens.

27. The endoscope of claim 26, in which the lens is a liquid crystal lens.

28. An endoscope suitable for autoclave sterilization, the endoscope comprising:
    an insertion section having an objective lens section disposed at one end of the insertion section for focusing a subject image;
    an image guiding fiber, disposed in said inserting section and having first and second ends, the first end being mounted adjacent said objective lens section for receiving said subject image;
    an eyepiece section located adjacent the second end of the image guiding fiber in a position to view the subject image provided via the image guiding fiber; and
    a sealing section disposed about the second end of the image guiding fiber and the eyepiece section and so formed as to prevent penetration of water vapor into spaces defined between and about the eyepiece section and the second end of the image guiding fiber when the endoscope is subjected to the autoclave sterilization, the endoscope further including a focusing structure that enables changing a relative distance between the eyepiece section and the second end of the image guiding fiber, the endoscope further including a lens that has an elastic, deformable shape and the focusing structure including an element that enables changing the shape of the lens.

29. An endoscope suitable for autoclave sterilization, the endoscope comprising:
    an insertion section having an objective lens section disposed at one end of the insertion section for focusing a subject image;
    an image guiding fiber, disposed in said inserting section and having first and second ends, the first end being mounted adjacent said objective lens section for receiving said subject image;
    an eyepiece section located adjacent the second end of the image guiding fiber in a position to view the subject image provided via the image guiding fiber; and
    a sealing section disposed about the second end of the image guiding fiber and the eyepiece section and so formed as to prevent penetration of water vapor into spaces defined between and about the eyepiece section and the second end of the image guiding fiber when the endoscope is subjected to the autoclave sterilization, the endoscope further including a focusing structure that enables changing a relative distance between the eyepiece section and the second end of the image guiding fiber, in which there is provided an exteriorly accessible space between the eyepiece section in the second end of the image guiding fiber and including a plurality of selectable lenses insertable thereinto.

30. An endoscope suitable for autoclave sterilization, the endoscope comprising:
    an insertion section having an objective lens section disposed at one end of the insertion section for focusing a subject image;
    an image guiding fiber, disposed in said inserting section and having first and second ends, the first end being mounted adjacent said objective lens section for receiving said subject image;
    an eyepiece section located adjacent the second end of the image guiding fiber in a position to view the subject image provided via the image guiding fiber; and
    a sealing section disposed about the second end of the image guiding fiber and the eyepiece section and so formed as to prevent penetration of water vapor into spaces defined between and about the eyepiece section and the second end of the image guiding fiber when the endoscope is subjected to the autoclave sterilization, the endoscope further including a focusing structure that enables changing a relative distance between the eyepiece section and the second end of the image guiding fiber, the endoscope further including an adjusting ring that enables positioning of the eyepiece section relative to the second end of the image guiding fiber and including a structure that prevents rotation of the eyepiece section when the adjusting ring is operated.

31. An endoscope suitable for autoclave sterilization comprising:
   an endoscope main body having an insertion section which is inserted into a subject;
   an objective lens disposed at the extreme end of the insertion section for focusing a subject image;
   an image guide fiber disposed in the endoscope main body and composed of an optical fiber bundle for transmitting the subject image focused by the objective lens; and
   an eyepiece section located on the base end of the endoscope main body, having an eyepiece lens unit for holding at least an eyepiece lens in a hermetically sealed space formed therein and a focus position changing structure which is constituted such that the eyepiece lens can move forward and rearward on an optical axis thereof in order to change the focus position of the eyepiece lens,
   wherein the eyepiece unit comprises:
      an eyepiece lens frame composed of a cylindrical metal member for holding the eyepiece lens therein;
      a first partition member connected to the extreme end of the eyepiece lens frame by metal welding and having a first optical path for passing the subject image transmitted by way of the image guide fiber to the eyepiece lens; and
      a second partition member connected to the base end of the eyepiece lens frame by metal welding and having a second optical path for passing the subject image exiting from the eyepiece lens.

32. An endoscope suitable for autoclave sterilization according to claim 31, wherein at least a portion of the insertion section is formed using a flexible polymeric material acting as an outer sheath member.

33. An endoscope suitable for autoclave sterilization according to claim 31, wherein the first optical path comprises:
   a first optical member for passing the subject image transmitted by way of the image guide fiber to the eyepiece lens; and
   a first metalizing treatment part formed by metalizing the outer peripheral surface of the first optical member and fixed to the first partition member by metal welding.

34. An endoscope suitable for autoclave sterilization according to claim 33, wherein the second optical path comprises:
   a second optical member for passing the subject image exiting from the eyepiece lens; and
   a second metalizing treatment part formed by metalizing the outer peripheral surface of the second optical member and fixed to the second partition member by metal welding.

35. An endoscope suitable for autoclave sterilization comprising:
   an insertion section formed using a flexible polymeric material acting as an outer sheath member to be inserted into a subject;
   an objective lens disposed at the extreme end of the insertion section for focusing a subject image;
   an image guide fiber disposed in the insertion section and composed of an optical fiber bundle for transmitting the subject image focused by the objective lens;
   an operating section connected to the base end of the insertion section for operating the endoscope;
   an eyepiece section located on the base end of the operating section, having an eyepiece lens unit for holding at least one eyepiece lens in a hermetically sealed space formed therein and a focus position changing structure which is constituted such that the eyepiece lens can move forward and rearward on an optical axis thereof in order to change the focus position of the eyepiece lens,
   wherein the eyepiece lens unit comprises:
      an eyepiece lens frame composed of a cylindrical metal member for holding the eyepiece lens therein;
      a first partition member connected to the extreme end of the eyepiece lens frame by metal welding and having a first optical path for passing the subject image transmitted by way of the image guide fiber to the eyepiece lens; and
      a second partition member connected to the base end of the eyepiece lens frame by metal welding and having a second optical path for passing the subject image exiting from the eyepiece lens.

36. An endoscope suitable for autoclave sterilization comprising:
   an insertion section having a shell for protecting the outer peripheral surface at a watertight seal level such that the equivalent reference leak amount is larger than $1 \times 10^{-9} Pa \cdot m^3/s$ but not larger than $5 \times 10^{-7} Pa \cdot m^3/s$;
   an objective lens section disposed at the extreme end of the insertion section for focusing a subject image;
   an eyepiece section located on the base end of the endoscope and including at least an eyepiece lens;
   an image guide fiber disposed in the insertion section and composed of a flexible optical fiber bundle for transmitting the subject image focused by the objective lens section;
   an eyepiece lens unit disposed in the eyepiece section, in a manner that causes the eyepiece lens to confront the base end surface of the image guide fiber, and formed at an hermetic seal level such that the equivalent reference leak amount is not larger than $1 \times 10^{-9} Pa \cdot m^3/s$; and
   a focus position changing structure at the eyepiece section which allows changing the focus of the eyepiece lens.

* * * * *